(12) United States Patent
Okuda et al.

(10) Patent No.: US 9,433,558 B2
(45) Date of Patent: Sep. 6, 2016

(54) MEDICINE TRANSFUSION APPARATUS AND MEDICINE TRANSFUSION METHOD

(71) Applicant: Panasonic Corporation, Osaka (JP)

(72) Inventors: Akinobu Okuda, Nara (JP); Tsuyoshi Tojo, Osaka (JP); Tohru Nakamura, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 303 days.

(21) Appl. No.: 14/360,100

(22) PCT Filed: Mar. 25, 2013

(86) PCT No.: PCT/JP2013/002012
§ 371 (c)(1),
(2) Date: May 22, 2014

(87) PCT Pub. No.: WO2013/157203
PCT Pub. Date: Oct. 24, 2013

(65) Prior Publication Data
US 2014/0311621 A1  Oct. 23, 2014

(30) Foreign Application Priority Data
Apr. 18, 2012 (JP) .................. 2012-094346

(51) Int. Cl.
*B67C 3/26* (2006.01)
*A61J 1/20* (2006.01)
(Continued)

(52) U.S. Cl.
CPC ............... *A61J 1/2096* (2013.01); *A61J 3/002* (2013.01); *A61J 1/10* (2013.01); *A61J 1/201* (2015.05); *A61M 5/1782* (2013.01); *A61M 2209/045* (2013.01); *B65B 3/003* (2013.01)

(58) Field of Classification Search
CPC .................. B65B 43/54–43/60; B65B 3/003; A61J 1/2096; A61J 3/002
USPC ......... 141/27, 104, 144, 145, 148, 151, 241, 141/247, 329, 330
See application file for complete search history.

(56) References Cited

U.S. PATENT DOCUMENTS 2,645,171 A * 7/1953 Moreland ............... A23B 4/285
141/172
2,656,785 A * 10/1953 Gannon ................. A23B 4/285
141/329

(Continued)

FOREIGN PATENT DOCUMENTS

| | | |
|---|---|---|
| JP | 1-244759 | 9/1989 |
| JP | 2007-319382 | 12/2007 |

(Continued)

OTHER PUBLICATIONS

International Search Report issued Jun. 18, 2013 in International (PCT) Application No. PCT/JP2013/002012.

(Continued)

*Primary Examiner* — Timothy L Maust
*Assistant Examiner* — Randall Gruby
(74) *Attorney, Agent, or Firm* — Wenderoth, Lind & Ponack, L.L.P.

(57) ABSTRACT

A medicine mixing apparatus transfusing a medicine using a syringe includes a medicine cassette holding a medicine container, a lifting unit moving the medicine cassette upward and downward to a middle position or a lower position of a main body while maintaining a horizontal attitude of the medicine cassette, a first holding portion held by the main body, and a second driving unit which drives a plunger of the syringe held by the first holding portion to transfuse the medicine.

14 Claims, 23 Drawing Sheets

(51) Int. Cl.
*A61J 3/00* (2006.01)
*A61J 1/10* (2006.01)
*A61M 5/178* (2006.01)
*B65B 3/00* (2006.01)

(56) References Cited

U.S. PATENT DOCUMENTS

| | | | | |
|---|---|---|---|---|
| 3,807,467 | A * | 4/1974 | Tascher | A61J 1/2096 141/18 |
| 3,863,556 | A * | 2/1975 | Townsend | A23B 4/28 426/281 |
| 4,142,000 | A * | 2/1979 | Townsend | A23B 4/285 426/281 |
| 4,467,708 | A * | 8/1984 | Twiford | A21C 15/007 141/329 |
| 4,924,771 | A * | 5/1990 | Langen | A23B 4/28 99/533 |
| 4,998,570 | A * | 3/1991 | Strong | A61M 5/1782 128/DIG. 1 |
| 5,881,640 | A * | 3/1999 | R.ae butted.vsager | A23B 4/28 99/408 |
| 6,360,794 | B1 * | 3/2002 | Turner | G01N 35/1079 141/1 |
| 6,761,191 | B2 * | 7/2004 | Rosen | B67C 3/001 134/168 C |
| 8,191,339 | B2 * | 6/2012 | Tribble | A61J 3/002 53/281 |
| 8,211,082 | B2 * | 7/2012 | Hasegawa | A61J 1/2096 604/411 |
| 8,225,824 | B2 * | 7/2012 | Eliuk | B65B 3/003 141/192 |
| 8,276,623 | B2 * | 10/2012 | Van Vreeland | B01F 11/0008 141/104 |
| 8,286,671 | B1 * | 10/2012 | Strangis | B65B 7/28 141/104 |
| 8,297,320 | B2 * | 10/2012 | Giribona | B65B 43/465 141/2 |
| 8,522,832 | B2 * | 9/2013 | Lopez | A61J 1/2096 141/27 |
| D692,161 | S * | 10/2013 | Okuda | D24/220 |
| D695,906 | S * | 12/2013 | Okuda | D24/220 |
| 8,596,309 | B2 * | 12/2013 | Mizuno | A61J 3/002 141/104 |
| 8,807,177 | B2 * | 8/2014 | Strangis | B63C 9/0005 141/104 |
| 2006/0049209 | A1 * | 3/2006 | Baker | A61J 1/2089 222/252 |
| 2008/0114328 | A1 * | 5/2008 | Doherty | A61J 1/2096 604/414 |

FOREIGN PATENT DOCUMENTS

| | | |
|---|---|---|
| JP | 2010-509002 | 3/2010 |
| WO | 2008/058280 | 5/2008 |
| WO | 2011/118835 | 9/2011 |

OTHER PUBLICATIONS

Notification Concerning Transmittal of International Preliminary Report on Patentability issued Oct. 30, 2014 in International (PCT) Application No. PCT/JP2013/002012.

Notification of Transmittal of Translation of the International Preliminary Report on Patentability issued Oct. 30, 2014 in International (PCT) Application No. PCT/JP2013/002012.

* cited by examiner

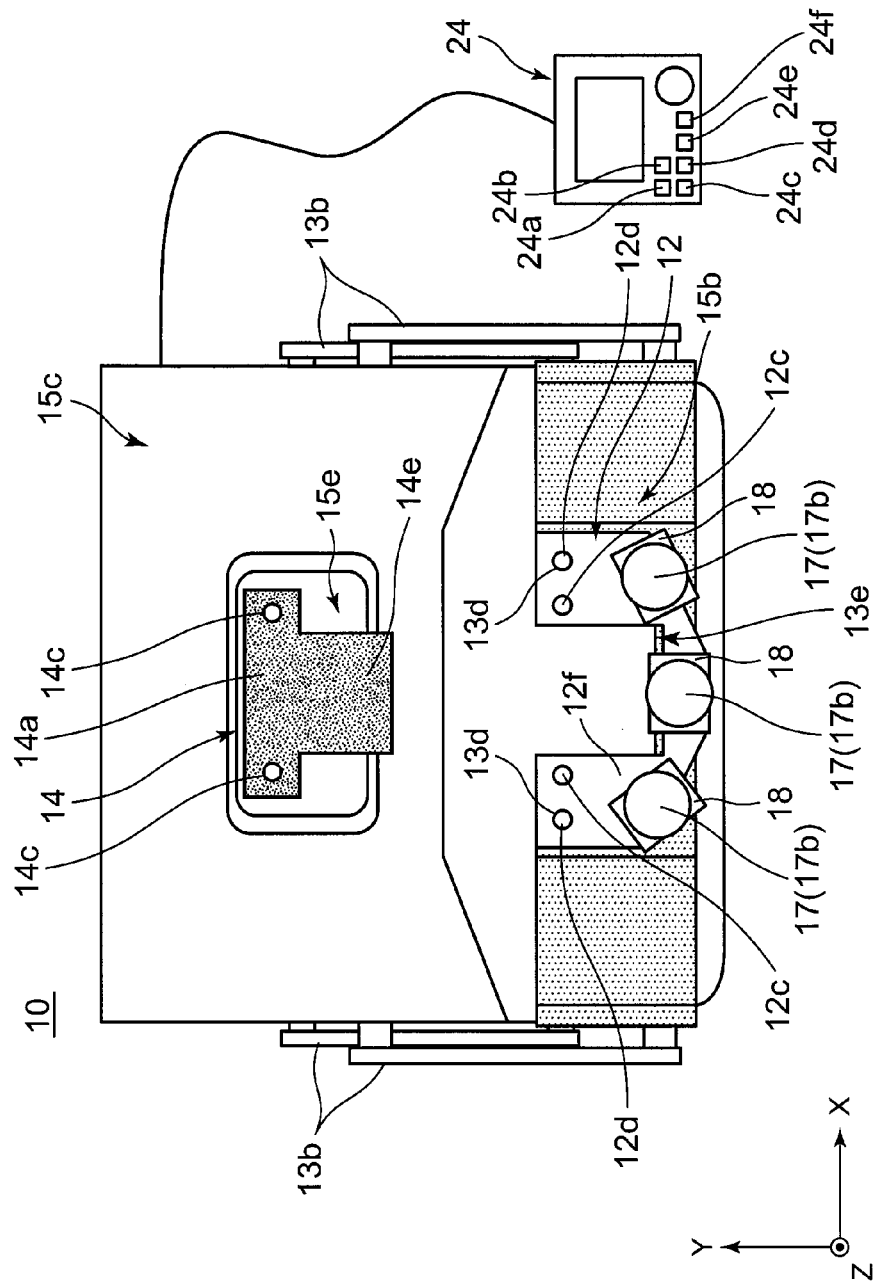

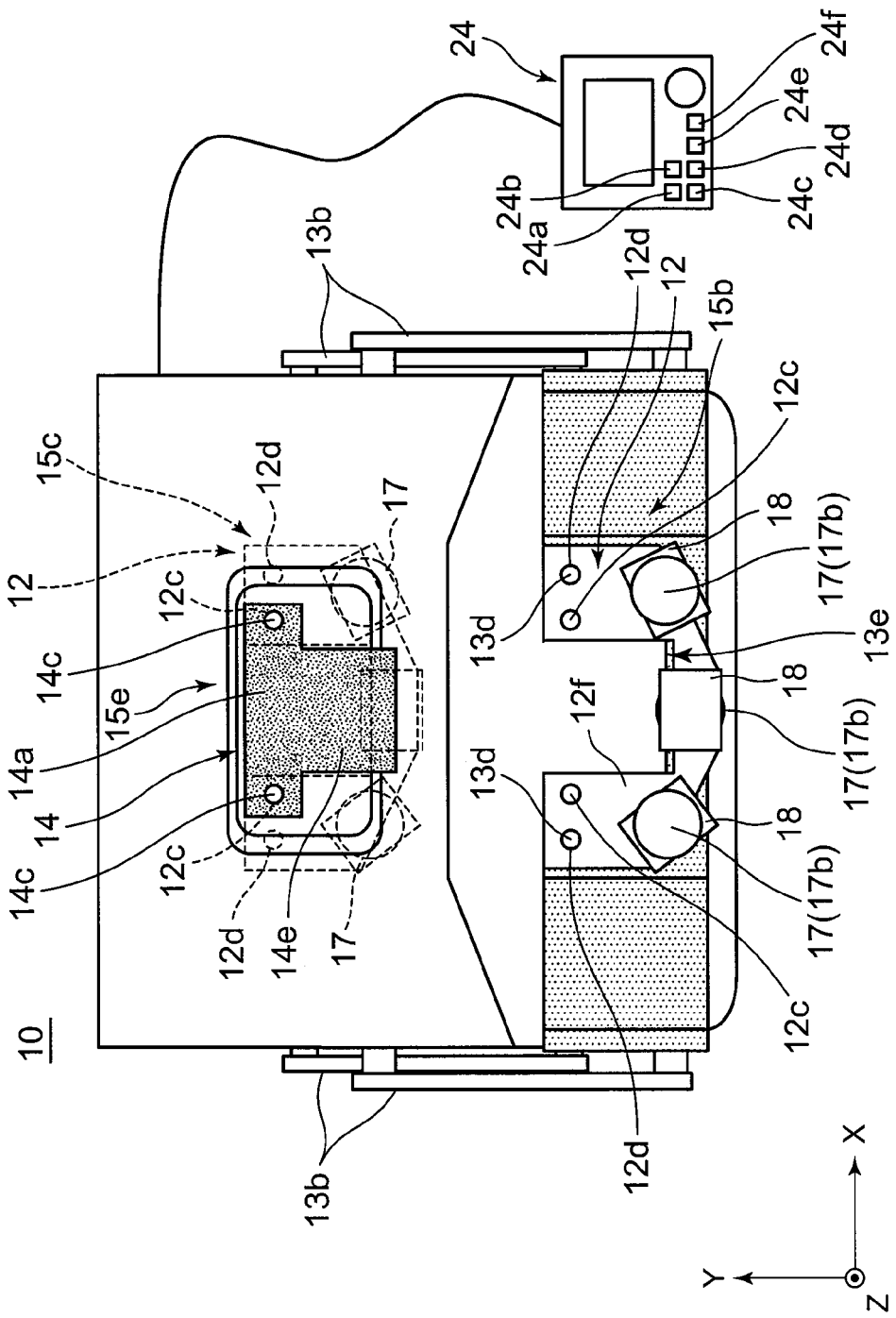

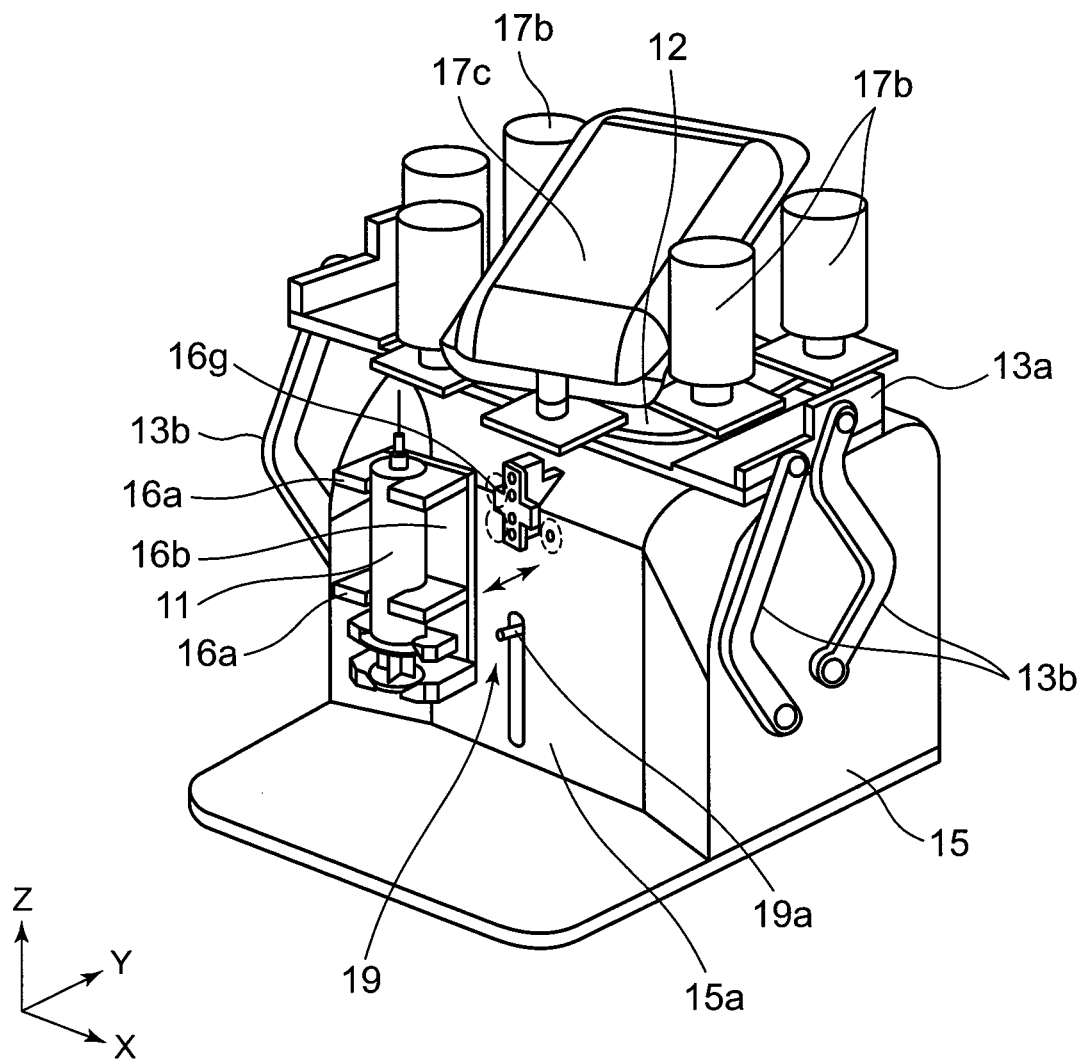

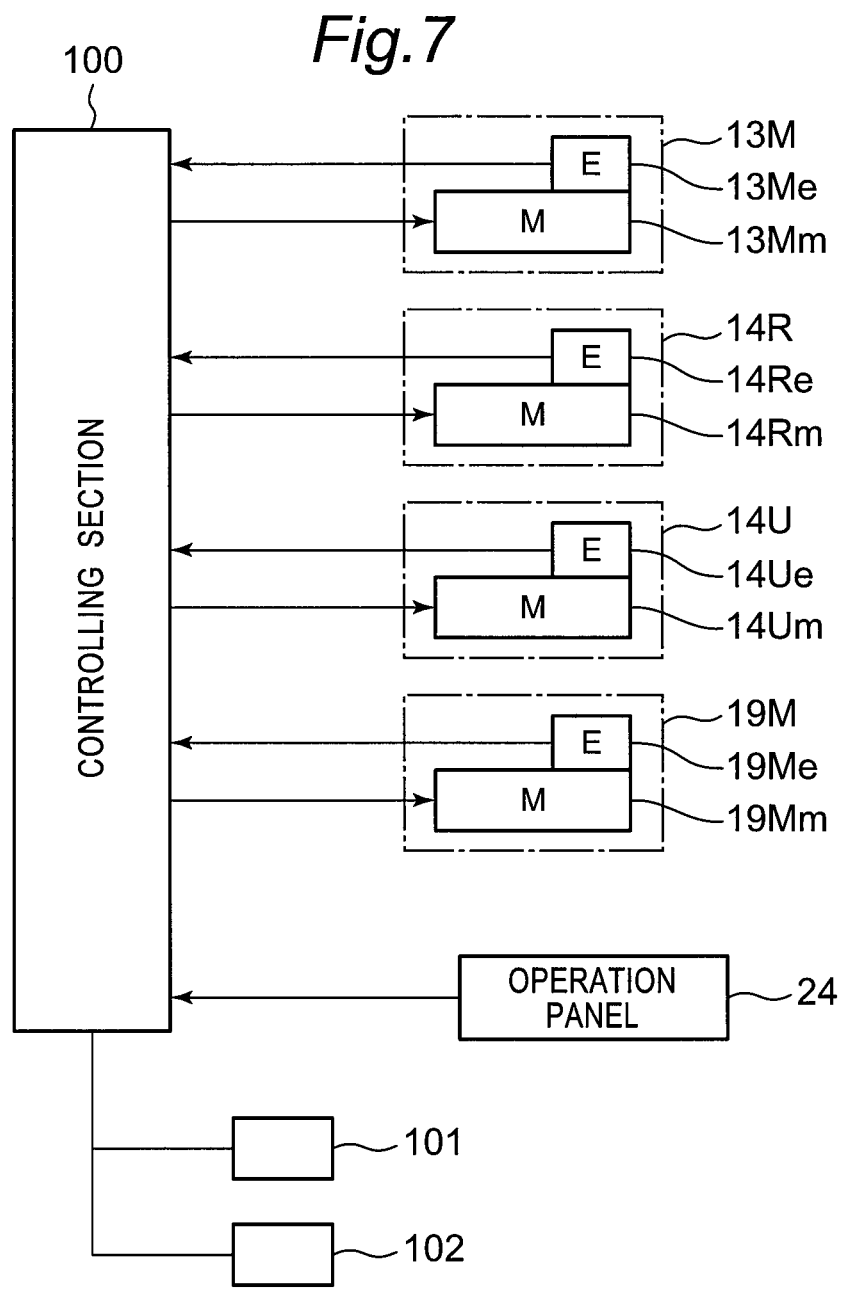

MEDICINE TRANSFUSION APPARATUS AND MEDICINE TRANSFUSION METHOD

TECHNICAL FIELD

The present invention relates to a medicine transfusion apparatus and a medicine transfusion method transfusing a medicine using a syringe.

BACKGROUND ART

In hospitals, medicines of several kinds taken out from different types of medicine containers may be mixed to prepare a mixture medicine, and the mixture medicine may be administered to inpatients, or the like. Such an operation of mixing medicines is usually performed manually by nurses or pharmacists (hereinafter referred to as an operator), for whom it is a heavy burden. In addition, the medicine containers that contain medicines have variety in type and shape. Also, in a case where an anticancer agent is dissolved by mixing with a liquid medicine, the mixture solution is harmful to humans and can be dangerous if the mixture solution leaks out from the medicine container to external air. Therefore, the mixing of medicines such as an anticancer agent needs to be operated in a work space of the hospital which is designed in consideration of safety (e.g. in a safety cabinet). In other words, operators are required to efficiently perform the mixing operation in the work space designed in consideration of safety. In order to ease such an operation, there has been suggested a device for safely and automatically sucking medicines from medicine containers (see, for example, Patent Literature 1).

FIG. 22 illustrates a structural view of a dispensing device of Patent Literature 1 as an example of a conventional medicine mixing device.

The dispensing device 1 illustrated in FIG. 22 is a device for dispensing radioisotope, i.e., a radioactive medicine that is hard to be handled. The dispensing device 1 dispenses a radioactive medicine from a storage container 4 located at the top of the device into a mixing container 5 located at the bottom of the device by moving an injection syringe 6 by means of a lifting mechanism 2 and a rotating mechanism 3. Radioactive medicines require to be handled with great care. Therefore, the storage container 4 is fixed to the device by a container holding portion 7 provided at the top of the device. The radioactive medicine is sucked into the injection syringe 6 by sticking a needle 6a of the injection syringe 6 into the storage container 4. Subsequently, the injection syringe 6 is moved to a position near the mixing container 5 by means of the lifting mechanism 2 and the rotating mechanism 3, and then the radioactive medicine is dispensed by discharging the radioactive medicine from the injection syringe 6 into the mixing container 5.

CITATION LIST

Patent Literature

Patent Literature 1: Unexamined Japanese Patent Publication No. H01-244759

SUMMARY OF INVENTION

Technical Problem

However, in the above described dispensing device 1, in order to dispense medicines, the injection syringe 6 needs to be moved or rotated in the vertical direction, and thus, there is a problem that the device is increased in size. When the device is increased in size, operators may not be able to perform medicine handling operation near a position on the operator's side.

In order to solve the above described problem, an object of the present invention is to provide a medicine transfusion apparatus and a medicine transfusion method, each of which is capable of being set in a limited space and capable of efficiently transfusing a medicine.

Solution to Problem

In order to achieve the above-described object, the present invention has the following construction.

In order to solve the above problem, a medicine transfusion apparatus according to an aspect of the present invention, is a medicine transfusion apparatus transfusing a medicine between a medicine container and a syringe by the syringe, the medicine transfusion apparatus comprising:

a medicine cassette that holds the medicine container;

a lifting unit that moves the medicine cassette upward and downward between a middle position on an upper portion and a lower position of a main body along an arcuate path while maintaining a horizontal attitude of the medicine cassette using a pair of parallel link mechanisms;

a first holding portion that is capable of holding the syringe and is detachably mounted to the main body;

a first driving unit that relatively moves the medicine cassette and the first holding portion so that a needle of the syringe held by the first holding portion is inserted into the medicine container; and a second driving unit that drives a plunger of the syringe to transfuse the medicine between the syringe and the medicine container.

In order to solve the above problem, a medicine transfusion method according to the present invention is a medicine transfusion method comprising:

a first step of moving a medicine cassette holding a medicine container upward from a lower position of a main body to a middle position on an upper portion of the main body along an arcuate path while maintaining a horizontal attitude of the medicine cassette by a lifting unit utilizing a pair of parallel link mechanisms;

a second step of reloading the medicine cassette from a first pedestal of the lifting unit to a second pedestal of a first driving unit in the middle position after the first step;

a third step of inserting a needle of a syringe held by a first holding portion into the medicine container held by the medicine cassette after the second step; and a fourth step of driving a plunger of the syringe to transfuse a medicine between the syringe and the medicine container after the third step.

Effects of Invention

According to each aspect of the present invention, a medicine transfusion apparatus and a medicine transfusion method, each of which is capable of being set in a limited space and capable of efficiently transfusing the medicine and a medicine transfusion method can be achieved.

BRIEF DESCRIPTION OF DRAWINGS

These and other objects and features of the present invention will become clear from the following description taken in conjunction with the preferable embodiments thereof with reference to the accompanying drawings, in which:

FIG. 2A is a plan view of the medicine mixing device according to the first embodiment of the present invention;

FIG. 2B is a plan view of the medicine mixing device according to the first embodiment of the present invention, in which a state where a medicine cassette is positioned in a middle position in FIG. 2A is illustrated by dotted lines (illustration of a pedestal is omitted);

FIG. 6 is a perspective view of the medicine mixing device according to the first embodiment of the present invention illustrating a state just before the first holding portion is mounted on a main body;

FIG. 7 is a block diagram illustrating the relationship between a controlling section and each driving unit etc. of the medicine mixing device according to the first embodiment of the present invention;

DESCRIPTION OF EMBODIMENTS

Figure 1:
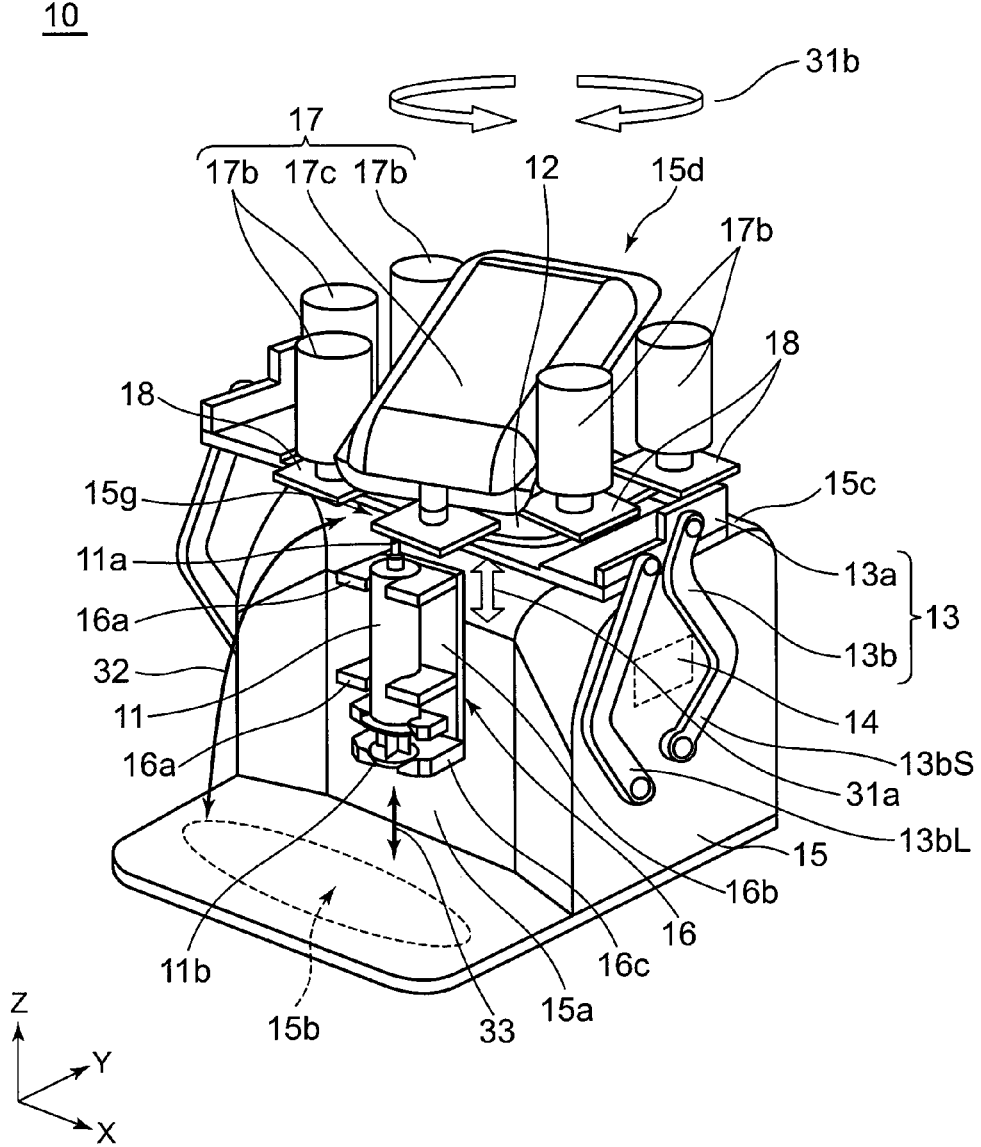
FIG. 1 is a perspective view showing a schematic construction of a medicine mixing device according to a first embodiment of the present invention.

An embodiment of the present invention will be described with reference to the drawings. It should be noted that the same constituent elements will be given the same reference numerals, and description thereof will sometimes be omitted. For easy understanding, the drawings are schematic focusing on the constituent elements. Also, axes X, Y, and Z are given in each drawing to facilitate understanding of the relationship of each drawing.

First Embodiment

Figure 3:
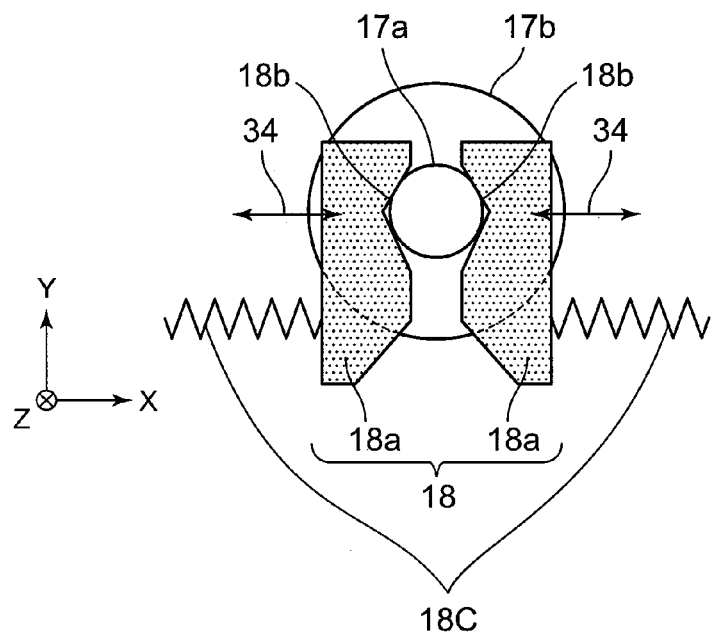
FIG. 3 is a bottom view showing a schematic construction of a second holding portion in the medicine cassette of the medicine mixing device according to the first embodiment of the present invention.
Figure 4:
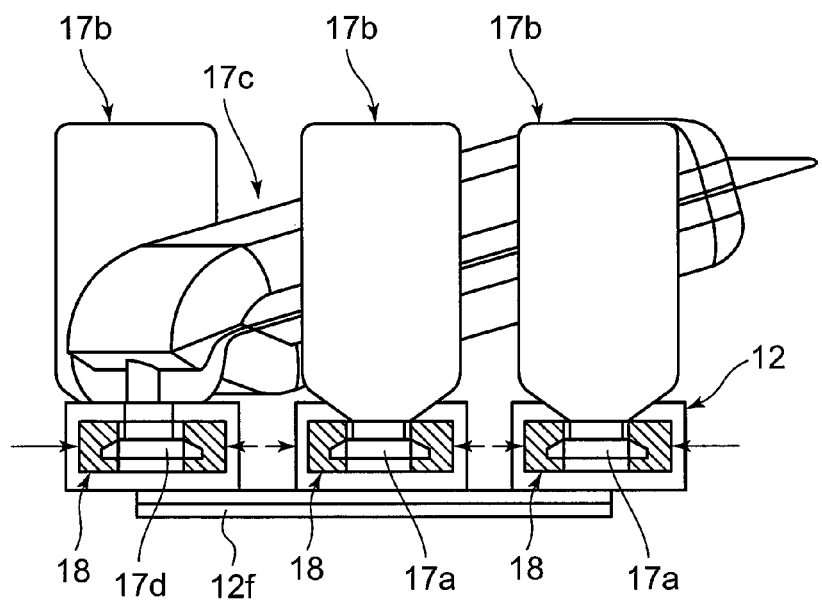
FIG. 4 is a side view including a partial cross section schematically illustrating a state where a medicine container is fixed to the medicine cassette.
Figure 5A:
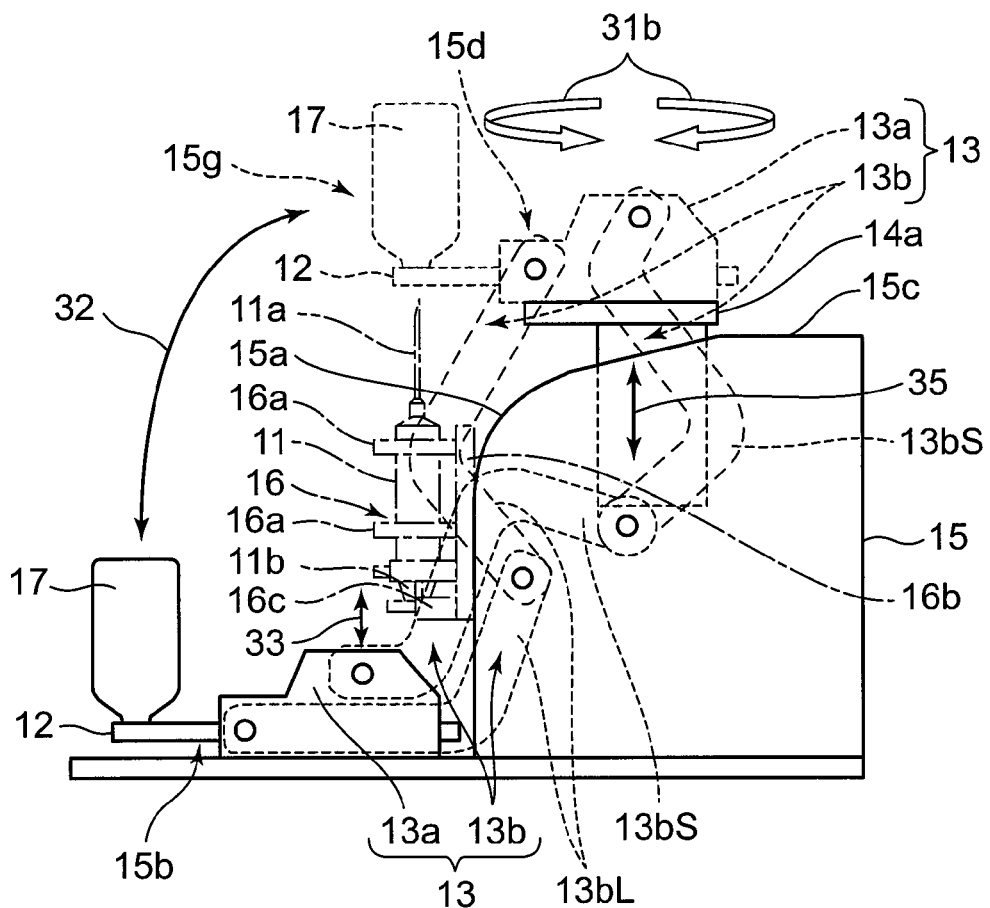
FIG. 5A is a side view outlining an operation in a lifting unit of the medicine mixing device according to the first embodiment of the present invention with a first holding portion being virtually illustrated.
Figure 5B:
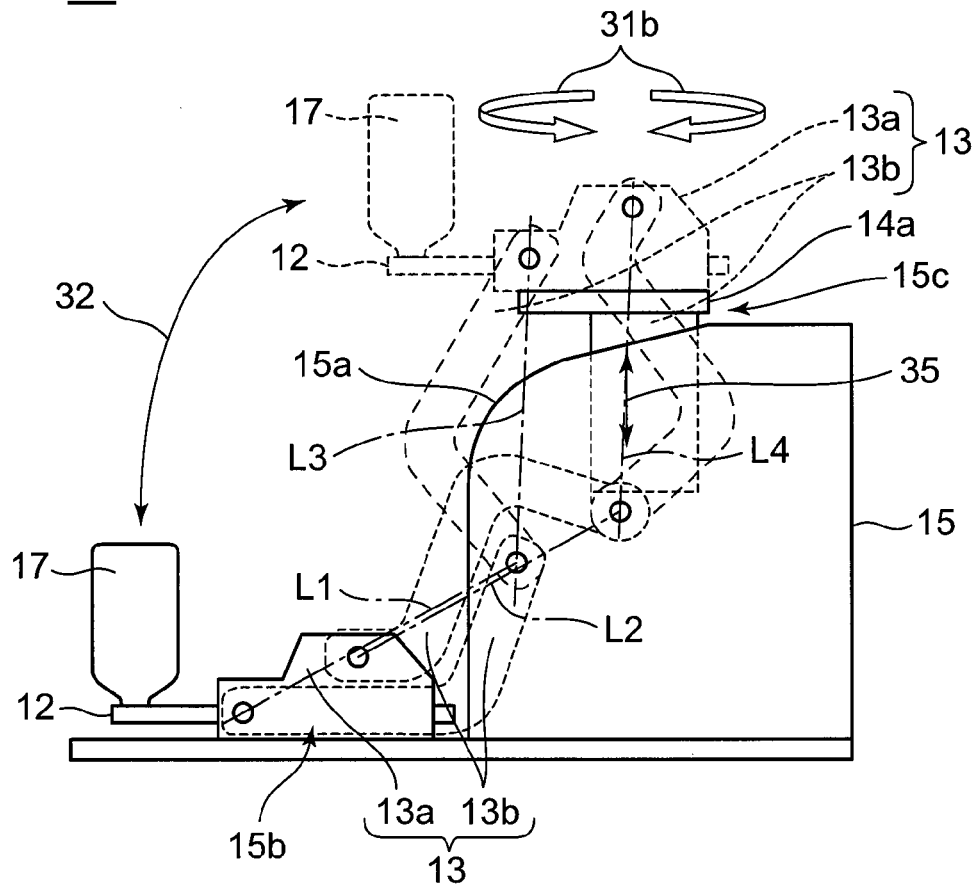
FIG. 5B is a side view outlining an operation in the lifting unit of the medicine mixing device according to the first embodiment of the present invention with the first holding portion being removed.

FIG. 1 is a perspective view showing a schematic construction of a medicine mixing device 10 according to a first embodiment of the present invention. FIG. 2A is a plan view of the medicine mixing device 10 according to the first embodiment. FIG. 2B is a plan view of the medicine mixing device 10, in which a state where a medicine cassette is positioned in a middle position in FIG. 2A is illustrated by dotted lines (illustration of a pedestal is omitted). FIG. 3 is a bottom view showing a schematic construction of a second holding portion 18 in a medicine cassette 12 of the medicine mixing device 10 according to the first embodiment. In should be noted that in FIGS. 2A and 2B, illustration of a syringe 11 and a first holding portion 16 is omitted. FIG. 4 is a side view including a partial cross section schematically illustrating a state where medicine containers 17 are fixed to the medicine cassette 12. FIG. 5A is a side view for outlining operation in a lifting unit 13 of the medicine mixing device 10 according to the first embodiment with the first holding portion 16 being virtually illustrated. FIG. 5B is a side view for outlining operation in the lifting unit 13 of the medicine mixing device 10 according to the first embodiment with the first holding portion 16 being removed. The medicine mixing device 10 according to the first embodiment is a medicine mixing device mixing a medicine such as injection the medicine in the medicine container 17 using the syringe 11.

Here, the first holding portion 16 is one example of a syringe holder that holds the syringe 11, and the second holding portion 18 is one example of a port holder that holds a port portion 17a of the medicine container 17. The lifting unit 13 is one example of a cassette lifting unit that moves the medicine cassette 12 upward and downward between a lower position 15b and a middle position 15c. Herein, the lower position 15b is one example of a lower position where the medicine cassette 12 is to be set, and the middle position 15c is one example of a middle position where the medicine cassette 12 is to be delivered from a first pedestal 13a to a second pedestal 14a. Also, an upper position 15d described below is one example of a medicine transfusing position, which is a home position where the transfusion of the medicine is performed in the first embodiment. Further, the medicine mixing device 10 is one example of a medicine transfusion apparatus transfusing the medicine, according to the first embodiment of the present invention, and a medicine transfusion method in the description below is one example of a medicine transfusion method transfusing the medicine, according to the first embodiment of the present invention. Further, a person, e.g. a nurse or a pharmacist, who performs the operation, is referred to as an operator.

As illustrated in FIG. 1, the medicine mixing device 10 of the first embodiment includes the medicine cassette 12, the lifting unit 13, a first driving unit 14, a main body 15, the first holding portion 16, and a second driving unit 19 (see FIG. 6). The first driving unit functions as one example of a vertical driving mechanism, and is one example of a cassette driving unit driving the medicine cassette 12. The second driving unit 19 is one example of a plunger driving unit driving a plunger 11b of the syringe 11.

Figure 13:
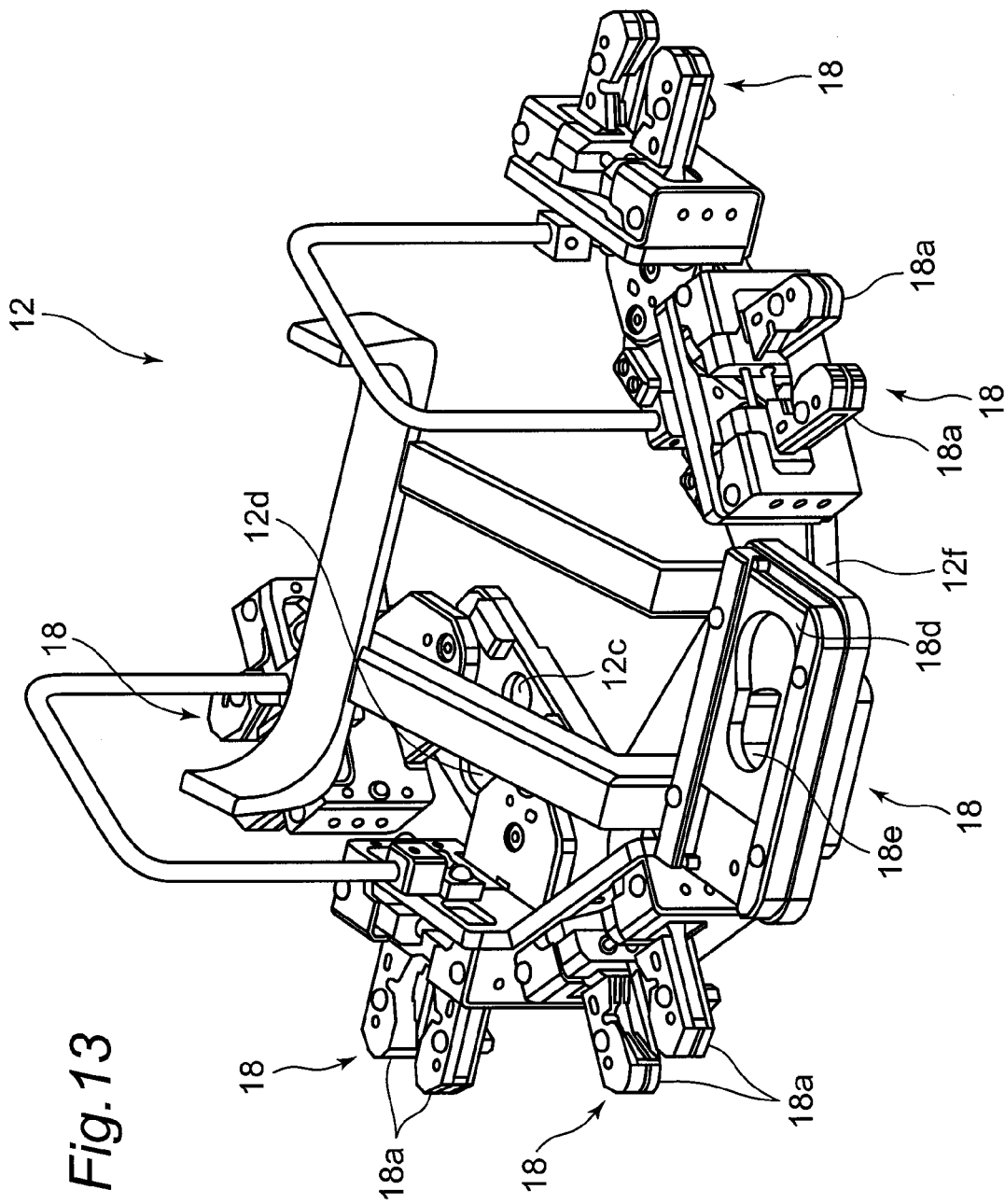
FIG. 13 is a perspective view illustrating the medicine cassette of the medicine mixing device according to the first embodiment of the present invention in a state where the medicine container is not held.

As illustrated in FIGS. 2A, 2B, and 13, the medicine cassette 12 is constructed by an arc-shaped fixing unit 12f. FIG. 13 is a perspective view of the medicine cassette 12. The fixing unit 12f has a pair of position regulating holes 12c disposed at the inner-side portion on both ends of an arc-shaped member, and a pair of position regulating holes 12d, each disposed at the outer-side portion of the pair of position regulating holes 12c. Further, the fixing unit 12f includes a plurality of the second holding portions 18 provided along the circumferential direction. Each one of the plurality of the second holding portion 18 is capable of holding one of a plurality of the medicine containers 17. The medicine cassette 12 is positioned with respect to the first pedestal 13a and detachably placed on the first pedestal 13a in such a manner that a pair of positioning pins 13d of the first pedestal 13a in the lifting unit 13 is fitted with respect to the pair of the position regulating holes 12d of the fixing unit 12f.

The first driving unit 14 moves upward the medicine cassette 12 held in the middle position 15c on an upper portion of the main body 15 up to the upper position 15d, and moves the medicine cassette 12 in a vertical direction 31a and in a rotating direction 31b. Further, the first driving unit 14 includes a first driving unit 14U (see FIG. 7) including a motor 14Um and an encoder 14Ue, a second driving unit 14R including a motor 14Rm and an encoder 14Re, and the second pedestal 14a having a T-plate shape.

The first driving unit 14U allows the T-plate shaped second pedestal 14a to vertically move upward and downward and to bring into contact with the fixing unit 12f of the medicine cassette 12. A projection 14e formed at the front side of the T-plate shaped second pedestal 14a is configured to vertically pass through a notch 13e of the first pedestal 13a in the lifting unit 13 (see FIG. 2A). By passing through the notch 13e, the second pedestal 14a is capable of lifting the fixing unit 12f of the medicine cassette 12 that is detachably placed on the first pedestal 13a upward from the first pedestal 13a. When the medicine cassette 12 is reloaded from the first pedestal 13a onto the second pedestal 14a, in the first embodiment, the pair of positioning pins 13d of the first pedestal 13a is disengaged from the pair of position regulating holes 12d of the medicine cassette 12, and a pair of positioning pins 14c of the second pedestal 14a is fitted into the pair of position regulating holes 12c of the medicine cassette 12. The medicine cassette 12 positioned in the middle position 15c can be reloaded from the first pedestal 13a onto the second pedestal 14a by utilizing the notch 13e. The pair of positioning pins 14c is stood upward at both ends of a base part side of the second pedestal 14a. The pair of positioning pins 14c is configured to be engageable to or disengageable from the pair of position regulating holes 12c of the medicine cassette 12 in the middle position 15c. The second driving unit 14R and the first driving unit 14U are provided with detectors (see FIG. 7) including the encoders 14Ue and 14Re that detect signals (e.g. rotational angle signals of motor shafts) outputted from the respective motors 14Rm and 14Um. On the basis of the signals detected by the encoders 14Ue and 14Re, the second driving unit 14R and the first driving unit 14U respectively control the rotation driving of the motors 14Rm and 14Um in forward and reverse directions in a controlling section 100, thereby performing predetermined moving up-down operation and rotating operation.

In the first driving unit 14U, the fixing unit 12f of the medicine cassette 12 is reloaded from the first pedestal 13a onto the second pedestal 14a to move the medicine cassette 12 from the middle position 15c to the upper position 15d. After that, the medicine cassette 12 is moved upward integrally with the second pedestal 14a in the vertical direction 31a, and then, the medicine cassette 12 is moved to the upper position 15d. In the upper position 15d, the medicine cassette 12 is driven up and down by the first driving unit 14 in the vertical direction 31a parallel to an arrow 35, and is driven to rotate in the rotating direction 31b. The medicine cassette 12 inserts and ejects a needle 11a of the syringe 11 with respect to the medicine container 17 by being driven up and down in the vertical direction 31a. Further, the medicine cassette 12 changes the position of each of the plurality of the medicine containers 17 with respect to the needle 11a of the syringe 11 by being driven to rotate in the rotating direction 31b. Here, the upper position 15d, which is the home position, is a position where the entire medicine cassette 12 including the port portion 17a of the medicine container 17 can be rotated in the rotating direction 31b without interfering with the tip of the needle 11a of the syringe 11. On the other hand, after the transfusion of the medicine is completed, the second pedestal 14a and the medicine cassette 12 are integrally moved downward from the upper position 15d to the middle position 15c. Then, the pair of positioning pins 13d of the first pedestal 13a is fitted into the pair of position regulating holes 12d of the medicine cassette 12, and the pair of positioning pins 14c of the second pedestal 14a is passed downward through the pair of position regulating holes 12c of the medicine cassette 12, thereby delivering the medicine cassette 12.

As illustrated in FIG. 4, an example of the medicine container 17 includes a plurality of vial bottles 17b, or an infusion bag 17c. Each medicine container 17 contains a medicine for being mixed or transfused. Each of the port portions 17a and a port portion 17d of the medicine container 17 is fixed to the second holding portion 18. That is, as illustrated in FIGS. 3 and 4, the port portion 17a of the vial bottle 17b and the port portion 17d of the infusion bag 17c are sandwiched from right and left sides by the second holding portions 18 of the medicine cassette 12, so that the plurality of the medicine containers 17 are held in an inverted position by the medicine cassette 12 with the port portions 17a and 17b being oriented downward.

Each of the second holding portions 18 includes, specifically as illustrated in FIGS. 3, 7, 13 and 14, a left and right pair of fixing plates 18a that is movable in conjunction with each other, and an elastic member 18C, such as a spring applying a biasing force toward the closing direction of the pair of fixing plates 18a. The left and right pair of fixing plate 18a has a recess 18b on an each opposing surface thereof where the port portions 17a and 17d can be held, and is configured to be movable in the direction of an arrow 34. It should be noted that FIG. 3 is a bottom view as seen from bottom to top of the second holding portion 18, and the vial bottle 17b is held in an inverted position by the second holding portion 18. The left and right pair of fixing plates 18a of the second holding portion 18 moves in conjunction with each other by a biasing force applied from the elastic member 18C in the direction of the arrow 34, by which the port portion 17a of the medicine container 17 is fixed or unfixed. In schematic illustrative views of FIGS. 2A and 2B, the port portions 17a of three medicine containers 17 (e.g. vial bottles 17b) are fixed to the respective second holding portions 18. Further, in FIGS. 13 and 14, the port portion 17d of the infusion bag 17c is engaged and held in such a manner that an engaging plate 18d is slidably fixed to the port portion 17d in an engaging hole 18e, the engaging hole 18e being another example of the second holding portion 18. For one example, in FIGS. 13 and 14, the port portion 17d of the infusion bag 17c is held at the center of the fixing unit 12f of the medicine cassette 12 by the engaging plate 18d of the second holding portion 18, and at each side of the engaging plate 18d, the port portions 17a of the plurality of vial bottles 17b are disposed to be held by a pair of the fixing plates 18a of the second holding portion 18.

Use of the medicine cassette 12 configured as described above allows the plurality of the medicine container 17 to be efficiently disposed in a small space in the medicine mixing device 10, and the desired medicine container 17 can be positioned at a medicine extraction position 15g by arcuately rotating the medicine cassette 12. As used herein, the medicine extraction position 15g is a position in the medicine mixing device 10, the position opposing the tip of the needle 11a of the syringe 11 held by the first holding portion 16.

Figure 15:
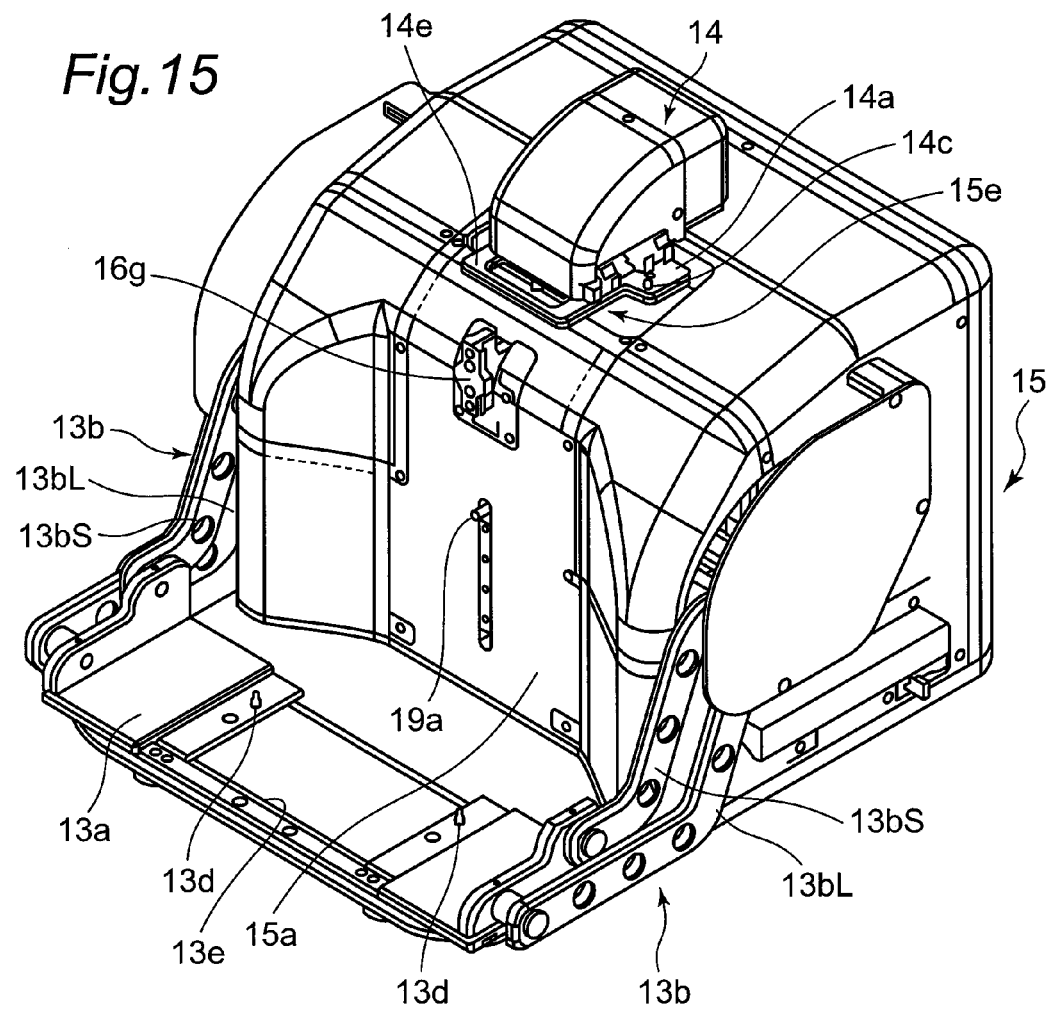
FIG. 15 is a perspective view of the medicine mixing device according to the first embodiment of the present invention in a state before the medicine cassette is set on the main body.
Figure 16:
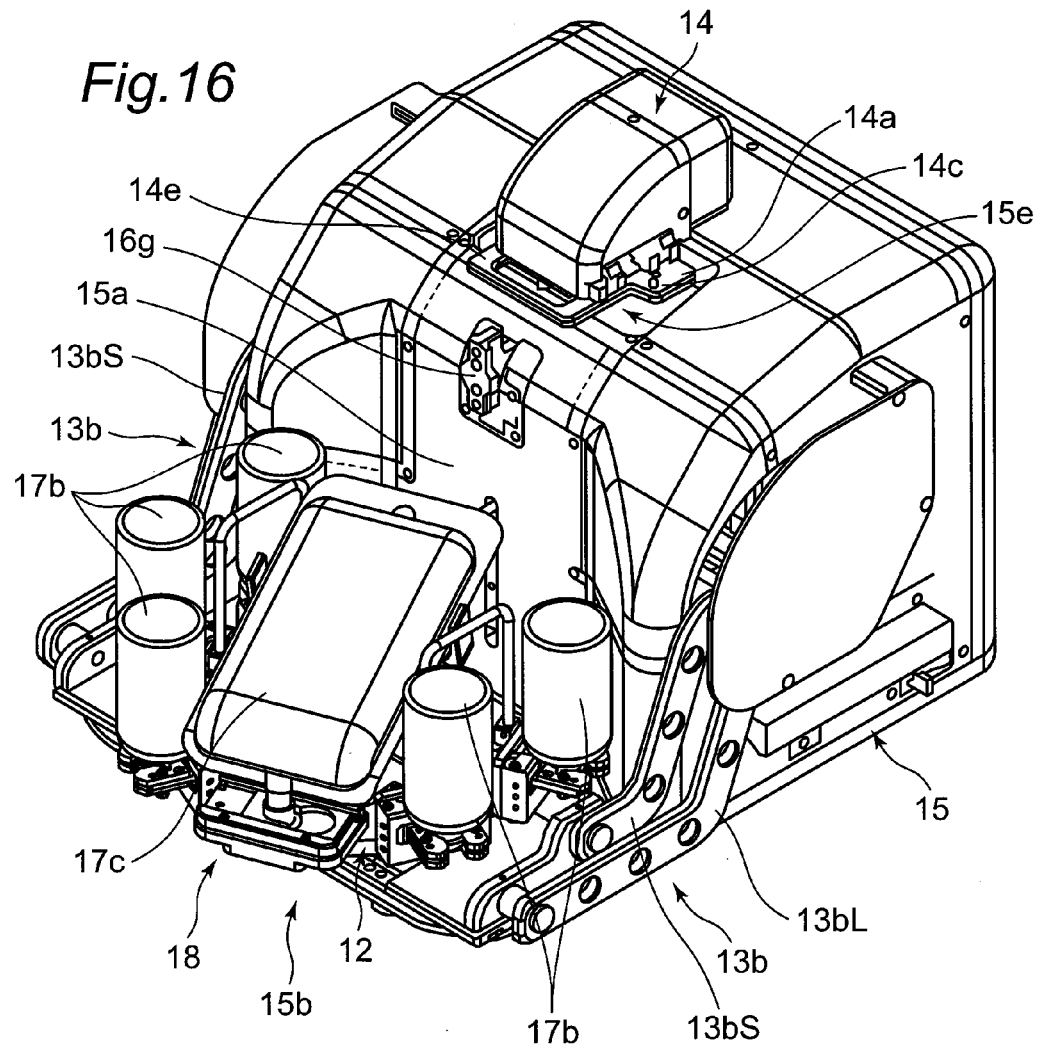
FIG. 16 is a perspective view of the medicine mixing device according to the first embodiment of the present invention in a state where the medicine cassette is set on the main body.
Figure 17:
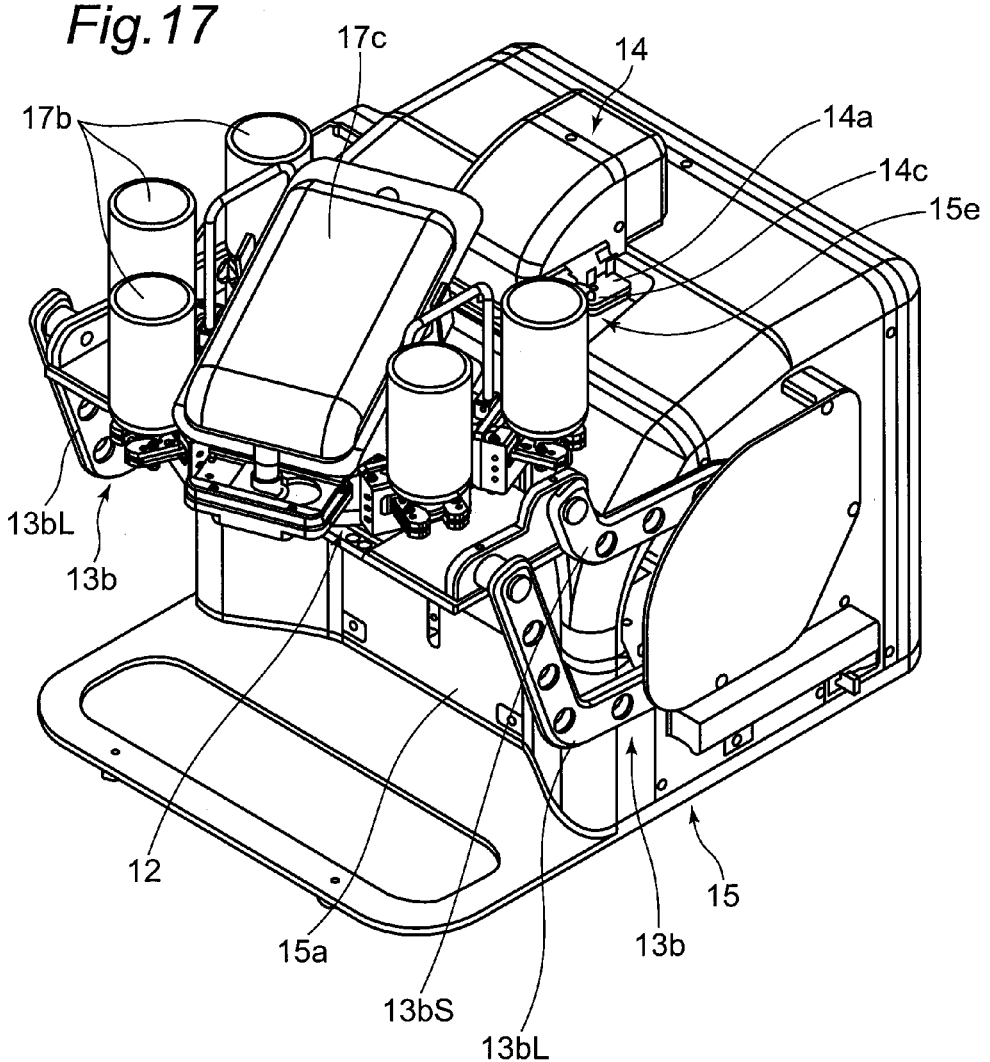
FIG. 17 is a perspective view of the medicine mixing device according to the first embodiment of the present invention in a state where the medicine cassette is moved upward from a lower position up to a middle position.

The lifting unit 13 includes, as illustrated in FIGS. 2A, 2B, and 15, the plate like first pedestal 13a having the notch 13e at the center thereof, a pair of parallel link mechanisms 13b each having one end being rotatably coupled to each side wall of the first pedestal 13a, and a fourth driving unit 13M (see FIG. 7). The fourth driving unit 13M is disposed in the main body 15, and includes an encoder 13Me and a motor 13Mm to which the other end of the pair of parallel link mechanisms 13b is each coupled so that the pair of parallel link mechanisms 13b is driven to rotate in forward and reverse directions in synchronism with each other. On the basis signals obtained by detecting the rotation angle of the motor 13Mm by the encoder 13Me or the like, the controlling section 100 controls the rotation driving of the motor 13Mm in forward and reverse directions, so that the pair of parallel link mechanisms 13b is rotated in clockwise or counterclockwise direction in synchronism with each other. When the pair of parallel link mechanisms 13b is rotated in synchronism with each other, it is ensured that the first pedestal 13a can be rotated and moved upward and downward in an arcuate direction indicated by an arrow 32 along the forward surface of the main body 15 and along the arcuate path between the lower position 15b and the middle position 15c on the forward side of the main body 15 (see FIGS. 16 to 18). At this time, since the pair of positioning pins 13d of the first pedestal 13a is fitted into the pair of position regulating holes 12d of the medicine cassette 12, the positioning is thereby maintained even though the medicine cassette 12 moves between the lower position 15b and the middle position 15c.

Here, as illustrated in FIG. 1, each of the parallel link mechanisms 13b of the first embodiment is constructed by a single S-shaped member 13bS and a single L-shaped member 13bL, which have shapes designed not to contact and interfere with each other during the rotating operation.

As seen from the drawings including FIG. 5A, in the lower position 15b, the parallel link mechanism 13b of the first embodiment is configured such that the L-shaped link 13bL is disposed vertically below the S-shaped link 13bS.

Also, as seen from the drawings including FIG. 5B, the parallel link mechanism 13b of the first embodiment has a shape where a line L1 and a line L2 are parallel to each other and form two sides of a parallelogram in the lower position 15b, and where a line L3 and a line L4 are parallel to each other and form two sides of a parallelogram in the middle position 15c. Here, the lines L1 to L4 are lines connecting between the centers of rotation of the portions each of which is rotatably coupled with the first pedestal 13a, the portions corresponding to the members holding the main body 15 and the medicine cassette 12 at the opposed ends of the L-shaped link 13bL and at the opposed ends of the S-shaped link 13bS.

Figure 9:
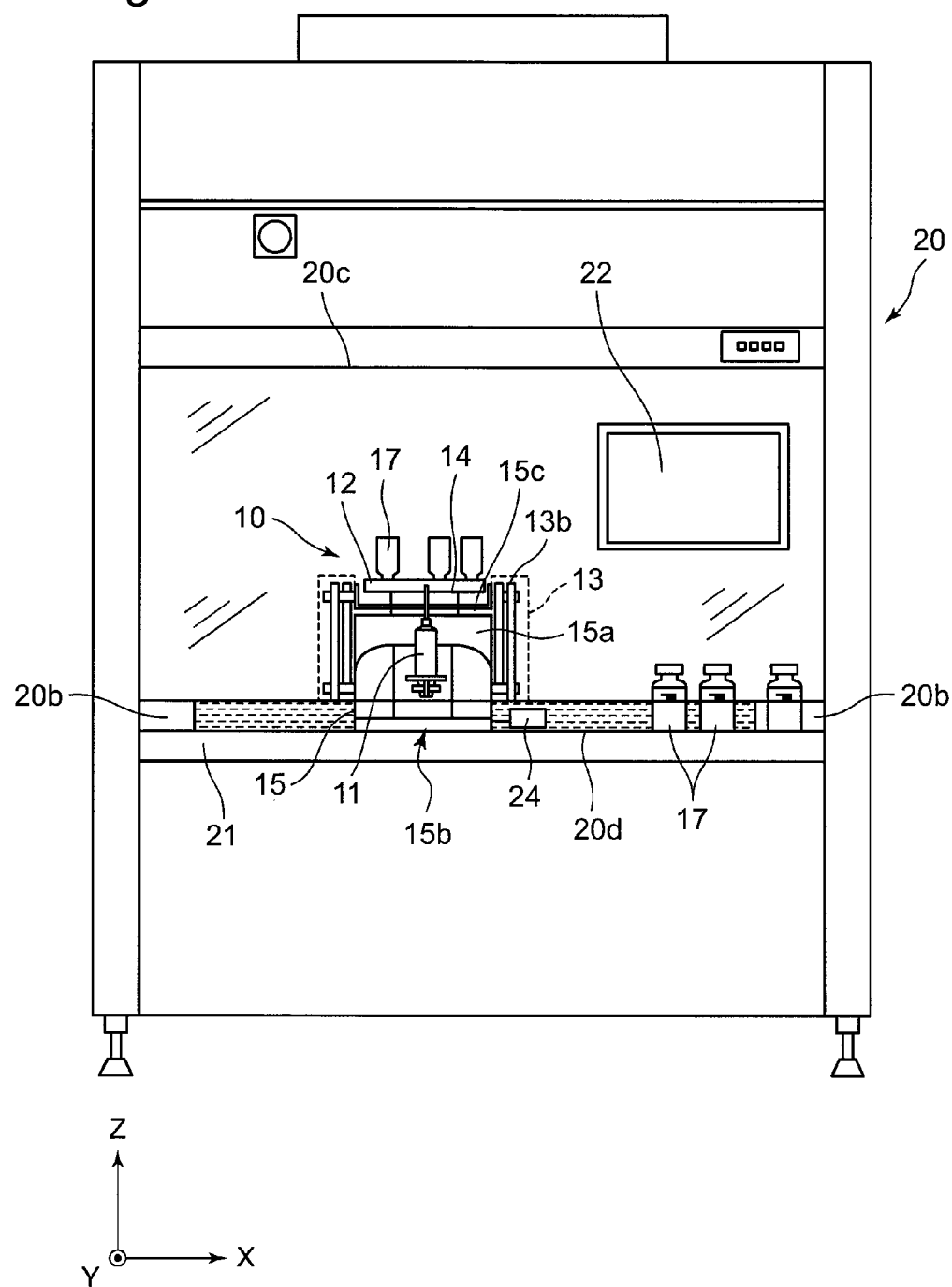
FIG. 9 is a front view illustrating an example, in which the medicine mixing device according to the first embodiment of the present invention is placed in a small space.

In the first embodiment, use of the S-shaped member 13bS and the L-shaped member 13bL configured as described above keeps the parallel link mechanism 13b out of the way of the operation as much as possible when an operator moves the first pedestal 13a of the lifting unit 13 to the lower position 15b to laterally remove the medicine cassette 12 from the main body 15. It should be noted that the lower position 15b of the main body 15 is, as illustrated in FIG. 9, positioned in the proximity of a workbench 21 of a safety cabinet 20, and is a position where the operator installs the medicine cassette 12 to the first pedestal 13a of the lifting unit 13 in the main body 15 and removes the medicine cassette 12 from the first pedestal 13a. Meanwhile, as illustrated in FIG. 9, the middle position 15c of the main body 15 is a position that is upwardly away from a working surface 21 of the safety cabinet 20, and is a position where the operation of mixing the medicine can be safely performed in a place away from the operator.

As described above, in the medicine mixing device 10 of the first embodiment, use of the pair of parallel link mechanisms 13b allows the medicine cassette 12 on the first pedestal 13a to be moved upward and downward along the arcuate path that extends along the proximity of a forward surface 15a of the main body 15, while maintaining the horizontal attitude of the medicine container 17 supported by the medicine cassette 12. The medicine container 17 supported by the medicine cassette 12 is moved upward and downward while maintaining the horizontal attitude, thereby allowing to prevent the medicine cassette 12 from falling out of the first pedestal 13a of the lifting unit 13 or preventing vibrations to the medicine in the medicine container 17 on the medicine cassette 12 and foaming of the medicine associated with the vibrations.

Figure 21:
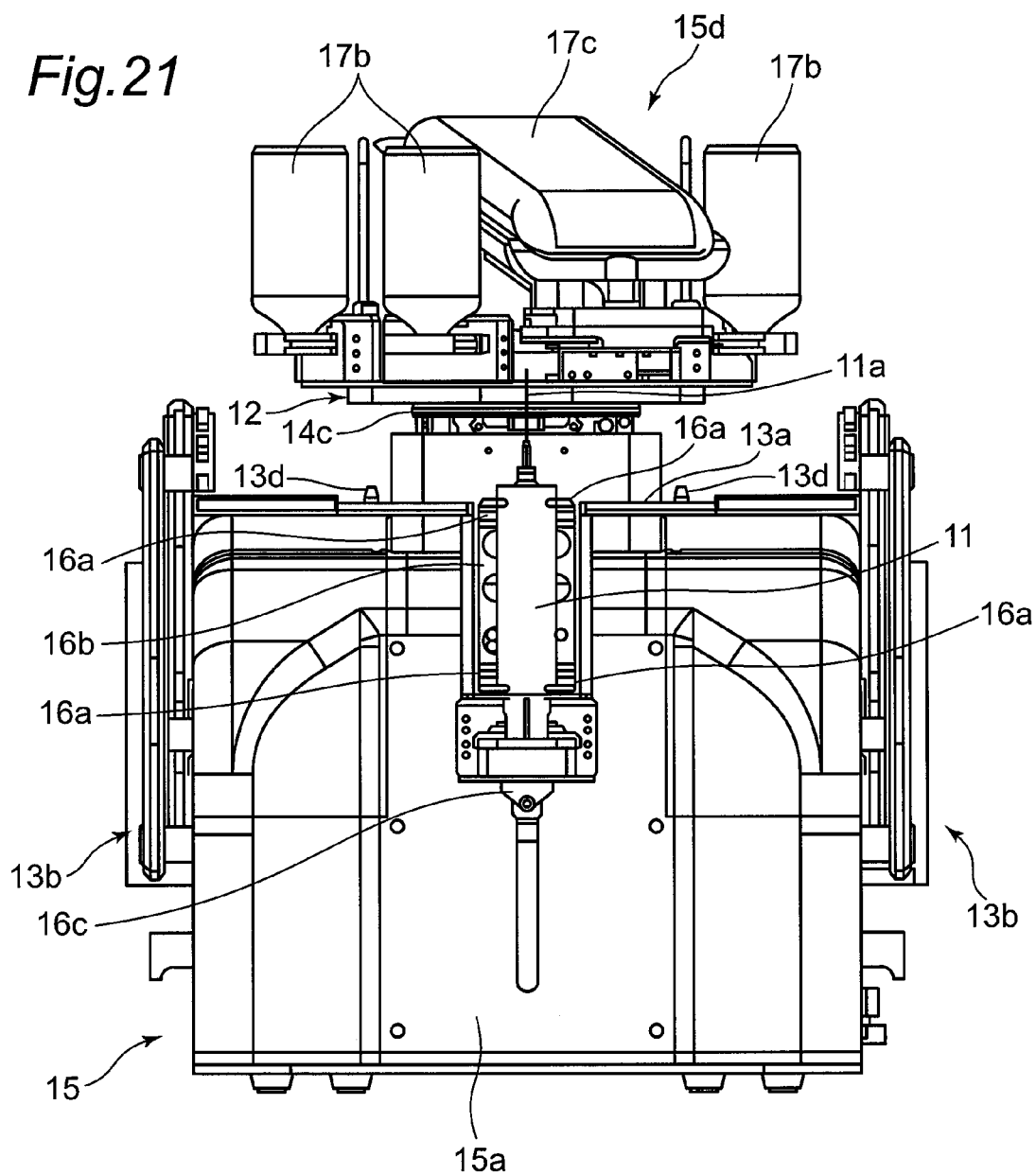
FIG. 21 is a perspective view of the medicine mixing device according to the first embodiment of the present invention in a state where the medicine cassette is moved up to an upper position, and in a state where the first holding portion is attached to the main body.
Figure 22:
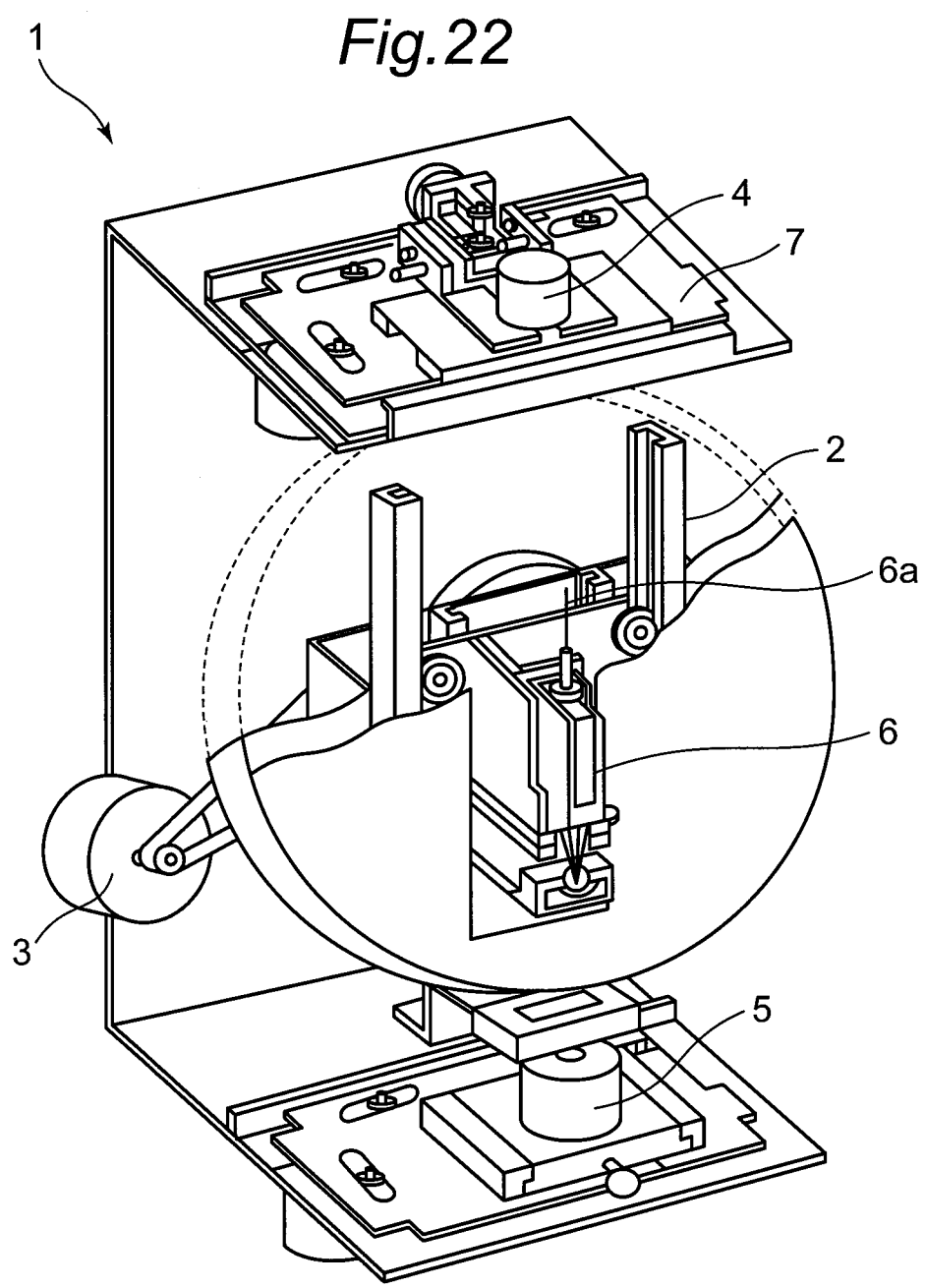
FIG. 22 is a structural view of a conventional medicine mixing device.

As illustrated in FIGS. 6 and 21, the first holding portion 16 is detachably held by the forward surface 15a of the main body 15 by detachably engaging an engaging hook (not illustrated) of the first holding portion 16 to an engaging groove 16g of the forward surface 15a. The first holding portion 16 includes: a base 16b in a plate-like shape; V-groove shaped claws 16a fixed at upper and lower portions of the base 16b, for detachably and laterally sandwiching and holding the syringe 11; and a coupling portion 16c coupled to a fifth driving unit 19M. The coupling portion 16c holds a plunger 11b of the syringe 11 and then, vertically moves integrally with the plunger 11b in the vertical direction of an arrow 33, and is coupled with a plunger driving pin 19a coupled to the fifth driving unit 19M in the main body 15. In order that the first holding portion 16 and the syringe 11 do not contact with the medicine cassette 12, in the first embodiment, the medicine cassette 12 is placed on the first pedestal 13a, and is moved from the lower position 15b up to the middle position 15c. After that, the first holding portion 16 is mounted on the main body 15. In other words, when the medicine cassette 12 is placed on the first pedestal 13a and is moved from the lower position 15b up to the middle position 15c, and conversely, is moved downward from the middle position 15c to the lower position 15b, the first holding portion 16 and the syringe 11 are removed from the main body 15. The configuration as described above realizes a reduction of the depth direction size of the entire device.

Figure 8:
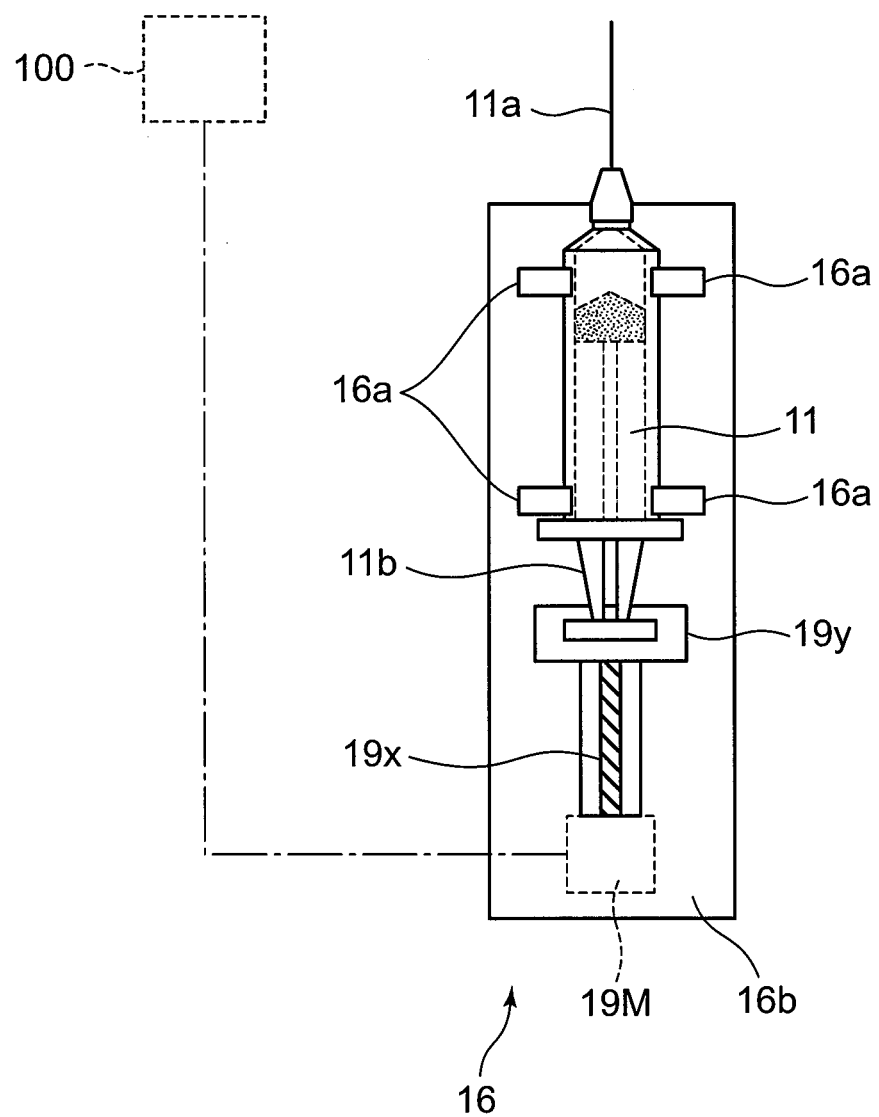
FIG. 8 is a schematic illustrative view for illustrating a driving mechanism of a syringe of the medicine mixing device according to the first embodiment of the present invention.

The second driving unit 19 includes the driving pin 19a coupling with the coupling portion 16c of the first holding portion 16, and the fifth driving unit 19M that vertically drives the driving pin 19a. The fifth driving unit 19M includes, for one example, as illustrated in FIGS. 7 and 8, a motor 19Mm, an encoder 19Me that detects signals (e.g. rotational angle signals of the motor shaft) outputted from the motor 19Mm so that the motor 19Mm can be controlled in the controlling section 100, a ball screw 19x that rotates in forward and reverse directions by the rotation of the motor 19Mm in forward and reverse directions, and a nut member 19y that vertically moves the ball screw 19x being threadably engaged therewith (see FIG. 7). In FIGS. 6 and 15, the driving pin 19a being coupled to the coupling portion 16c projects from the forward surface 15a of the main body 15, and the driving pin 19a is removably engaged with the plunger 11b. In a state where the driving pin 19a is coupled with the coupling portion 16c, the driving pin 19a is vertically driven by the rotation of the motor 19Mm in forward and reverse directions, thereby vertically driving the plunger 11b. The fifth driving unit 19M drives the plunger 11b via the driving pin 19a, so that the syringe 11 sucks a predetermined amount of medicine from the medicine container 17, or discharges the medicine from the syringe 11 to the medicine container 17.

As illustrated in FIG. 7, the medicine mixing device 10 further includes the controlling section 100. The controlling section 100 controls drives of the second driving unit 14R, the first driving unit 14U, the fourth driving unit 13M, and the fifth driving unit 19M on the basis of instructions inputted from an operation panel 24 to execute respective predetermined operations.

Further, the operation panel 24 (see FIGS. 2A and 2B) is disposed in the proximity of the lower position 15b of the medicine mixing device 10, the operation panel 24 allowing an operator to perform all the operations in proximity to the lower position 15b. The operation panel 24 has a delivery start button 24a, a setting completion button 24b, a mounting completion button 24c, a removal completion button 24d, a dispensing completion button 24e, and an operation completion button 24f.

The outline of the method mixing the medicine by using the medicine mixing device 10 of the first embodiment will now be briefly described.

First, in a state where the first holding portion 16 and the syringe 11 have not been mounted on the main body 15, an operator (e.g. a nurse or a pharmacist) sets the medicine cassette 12 on the first pedestal 13a of the lifting unit 13 in the lower position 15b of the main body 15 (see preparatory operation prior to Step S14 to be described later).

When the operator starts mixing the medicine by operating the operation panel 24 (see FIGS. 2A and 2B), the driving of the fourth driving unit 13M of the lifting unit 13 is controlled under the control from the controlling section 100, so that the medicine cassette 12 together with the first pedestal 13a is moved upward from the lower position 15b up to the middle position 15c of the main body 15 via the pair of parallel link mechanisms 13b (see Steps S14 and S15 to be described later).

After that, when the driving of the first driving unit 14U of the first driving unit 14 is controlled under the control from the controlling section 100, the medicine cassette 12 is reloaded from the first pedestal 13a to the second pedestal 14a, and then the medicine cassette 12 is moved upward from the middle position 15c up to the upper position 15d (see Steps S16 to S19 to be described later).

Next, the operator mounts the syringe 11 on the main body 15 together with the first holding portion 16.

After that, when the driving of the second driving unit 14R is controlled under the control from the controlling section 100, the medicine cassette 12 is rotated in the rotating direction 31b, so that the desired medicine container 17 (intended medicine container) is selected and disposed on the medicine extraction position 15g located directly above the needle 11a at the tip of the syringe 11 (see Steps S22-0 to S23 to be described later).

Next, when driving of the first driving unit 14U is controlled under the control from the controlling section 100, the medicine cassette 12 together with the second pedestal 14a is moved downward from the upper position 15d to a puncturing position, so that the needle 11a of the syringe 11 is inserted in the port portion 17a of the medicine container 17 positioned on the medicine extraction position 15g (see Steps S24 and S25 to be described later).

After that, when the driving of the fifth driving unit 19M is controlled under the control from the controlling section 100, the plunger 11b of the syringe 11 held by the first holding portion 16 is moved downward along the direction of the arrow 33, so that the medicine is sucked from the medicine container 17 into the syringe 11 transfusing and mixing (see Steps S26 and S27 to be described later).

Next, when the driving of the first driving unit 14U is controlled under the control from the controlling section 100, the medicine cassette 12 together with the second pedestal 14a is moved upward from the puncturing position up to the upper position 15d, so that the needle 11a of the syringe 11 is removed from the medicine container 17 (see Steps S28 and S29 to be described later).

After that, if the medicine from another medicine container 17 is further transfused into the syringe 11, the medicine container 17 (intended medicine container) is selected by rotating the medicine cassette 12 in the rotating direction 31b under the control from the controlling section 100, and then puncture operation and transfusion operation are performed again.

In such a manner as described above, the medicine in the medicine container 17 on the medicine cassette 12 is transfused to and mixed in the syringe 11.

FIG. 9 is a front view illustrating an example, in which the medicine mixing device 10 according to the first embodiment of the present invention is placed in a small space in a hospital or a dispensary or the like. In FIG. 9, the medicine mixing device 10 is disposed, for example, on the workbench 21 in the safety cabinet 20. In the first embodiment, the operator performs the mixing operation in a limited space of the safety cabinet 20 as illustrated in FIG. 9, in particular, in the space in proximity to the forward surface 15a and the middle position 15c of the main body 15 in the medicine mixing device 10.

On the forward surface of the safety cabinet 20, an opening 20b is provided, through which the operator's hand or the medicine container 17 can be taken in and out. Taking-in and -out of the medicine to the interior of the safety cabinet 20, or manipulation of the medicine mixing device 10 in the safety cabinet 20, and mounting and removal of the medicine container 17 to and from the medicine cassette 12 are available utilizing this opening 20b.

In the safety cabinet 20, clean air is flown downward from an upper portion 20c to a lower portion 20d so that cleanliness of the interior is maintained and no interior atmosphere leaks from the safety cabinet 20, and air is strongly taken in from an air inlet (not illustrated) provided on the workbench 21 positioned in the proximity of the opening 20b. Such an arrangement ensures cleanliness and safety of the interior of the safety cabinet 20.

The medicine mixing device 10 may also be associated with a server in the hospital (not illustrated) to display information on the medicine and medical care, information on manipulation of the medicine mixing device 10, or the like on a monitor 22 disposed in the interior of the safety cabinet 20.

In the first embodiment, the reason why it is possible to perform medicine mixing operation in such a small work space as illustrated in FIG. 9 is because the work space required for the medicine mixing operation using the medicine mixing device 10 of the first embodiment is configured to be fitted into a limited space around the lower position 15b of the main body 15. Therefore, the medicine mixing device 10 of the first embodiment allows operation of mixing the medicine, such as anticancer agents, which required to be operated in an enclosed space, to be safely performed, and thus is a mixing device (transfusing device) suitable for setting in a small work space. The medicine mixing device 10 of the first embodiment is particularly advantageous when being used in a safety cabinet, of which opening is disposed in the proximity of a lower portion (only the area approximately directly above a workbench). The reason is that the medicine mixing device 10 of the first embodiment allows all operations to be performed in the proximity of the lower position 15b of the main body 15.

Figure 10:
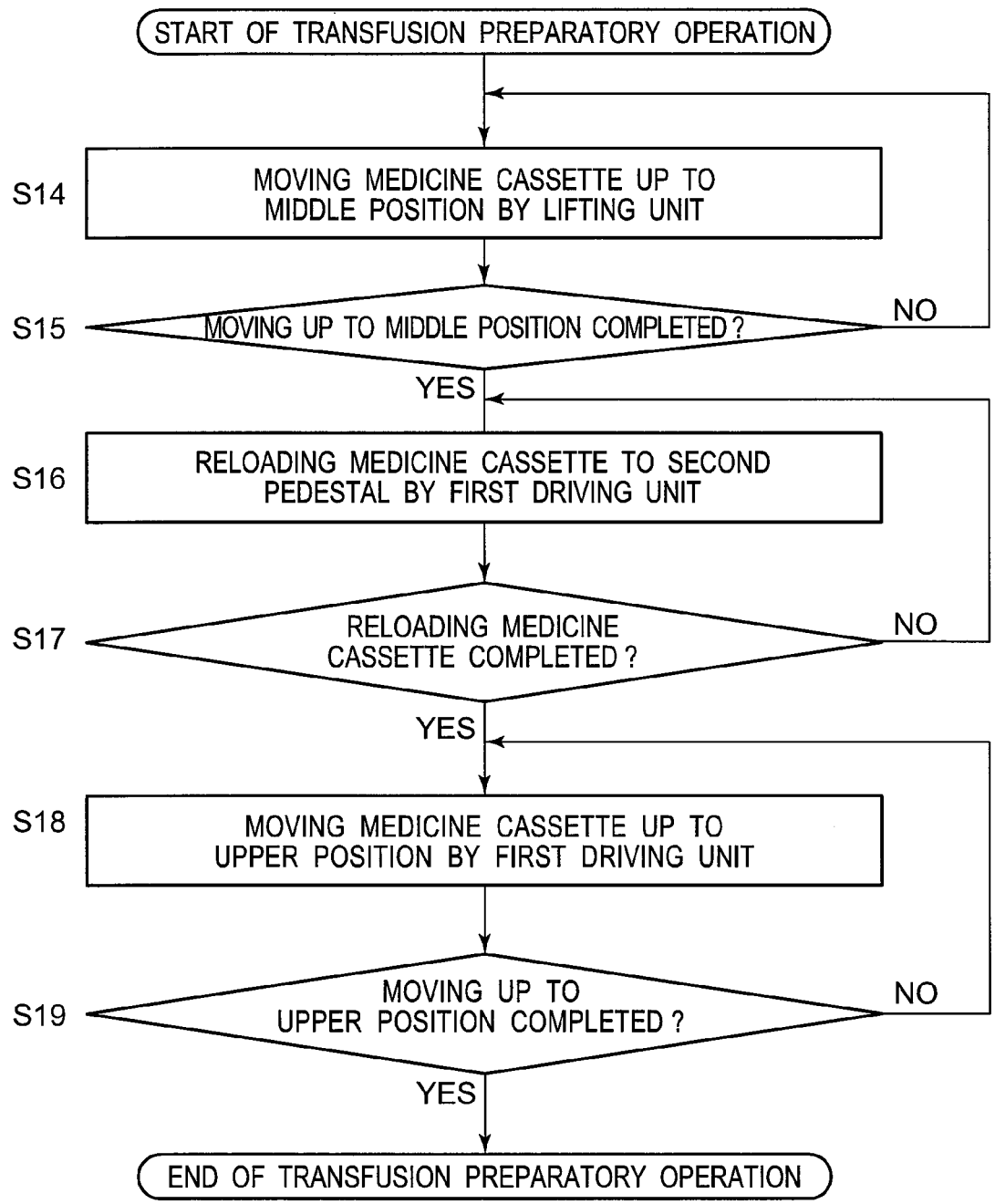
FIG. 10 is a specific flow chart illustrating a medicine mixing method according to the first embodiment of the present invention.
Figure 11:
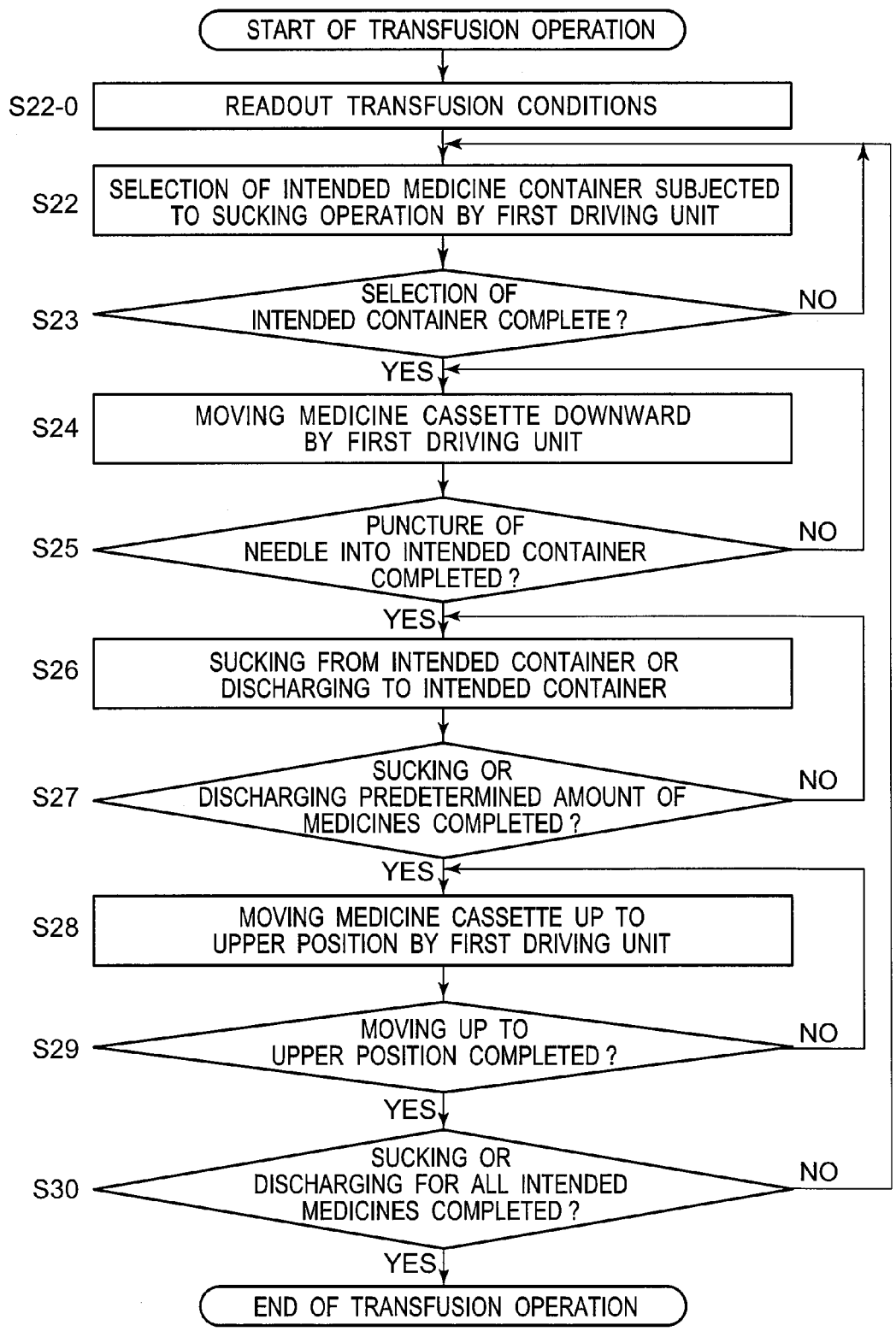
FIG. 11 is a specific flow chart illustrating the medicine mixing method according to the first embodiment of the present invention.
Figure 12:
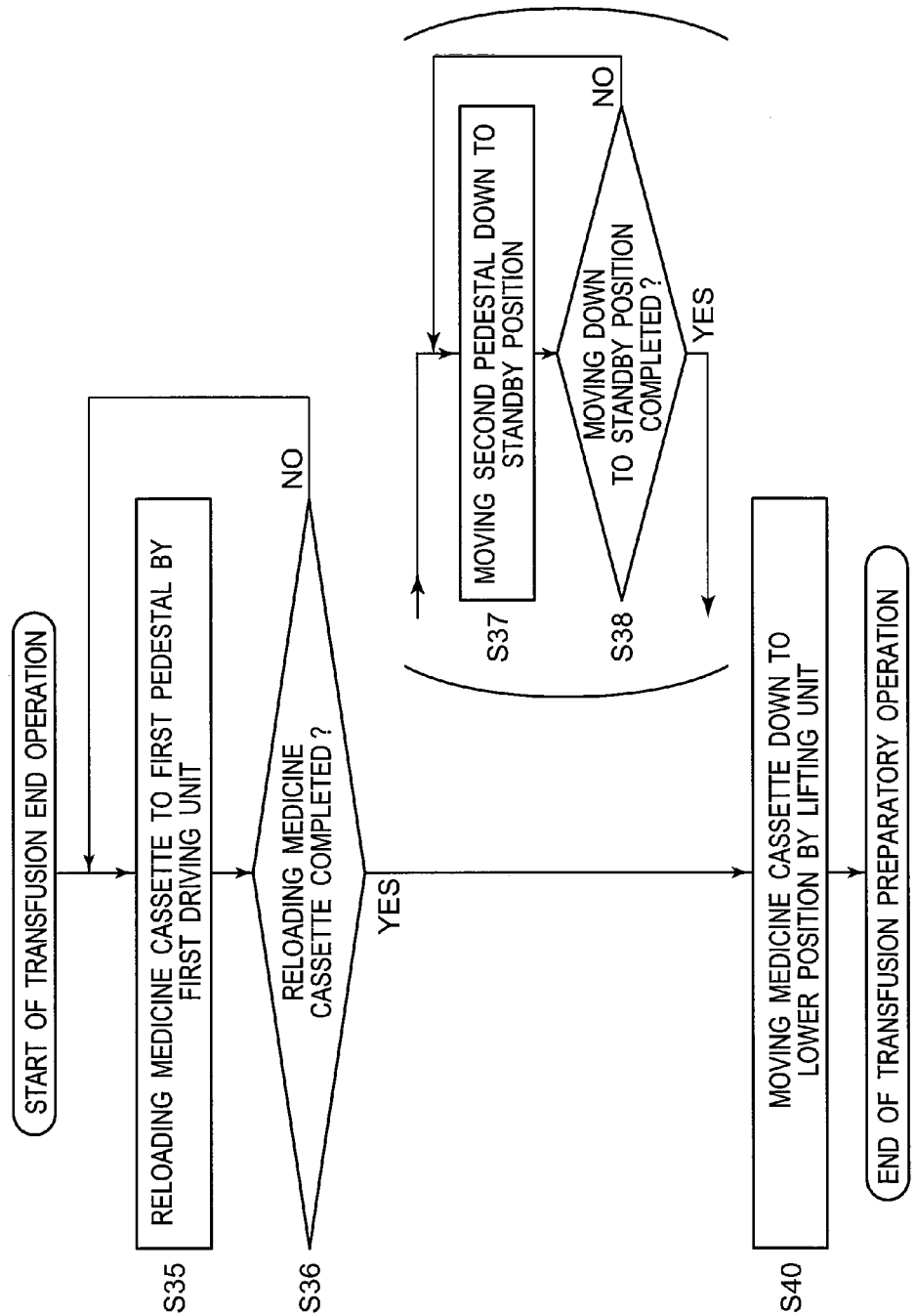
FIG. 12 is a specific flow chart illustrating the medicine mixing method according to the first embodiment of the present invention.

A medicine mixing method according to the first embodiment of the present invention using the above medicine mixing device 10 will now be specifically described with reference to flow charts. FIGS. 10, 11, and 12 are specific flow charts illustrating a medicine mixing method according to the first embodiment of the present invention, and illustrate transfusion preparatory operation, transfusion operation, and transfusion end operation. Hereinafter, a description will be given along these flow charts.

First, in order to initiate operation of the medicine mixing device 10, an operator depresses the delivery start button 24a on the operation panel 24. At this time, the operator causes the medicine cassette 12 to hold the medicine container 17 that is used for mixing, in the second holding portion 18. More specifically, as a cassette setting step performed by the operator (preparatory operation prior to Step S14 in FIG. 10), the medicine container 17 is set on the medicine cassette 12 such that the plurality of the medicine containers 17 are respectively held by the plurality of the second holding portions 18 in an inverted position (see FIG. 13). At this stage, the medicine cassette 12 is disposed separately from the medicine mixing device 10. When the delivery start button 24a is depressed, the first pedestal 13a of the lifting unit 13 moves to the lower position 15b of the medicine mixing device 10 and is brought into a standby state.

Figure 14:
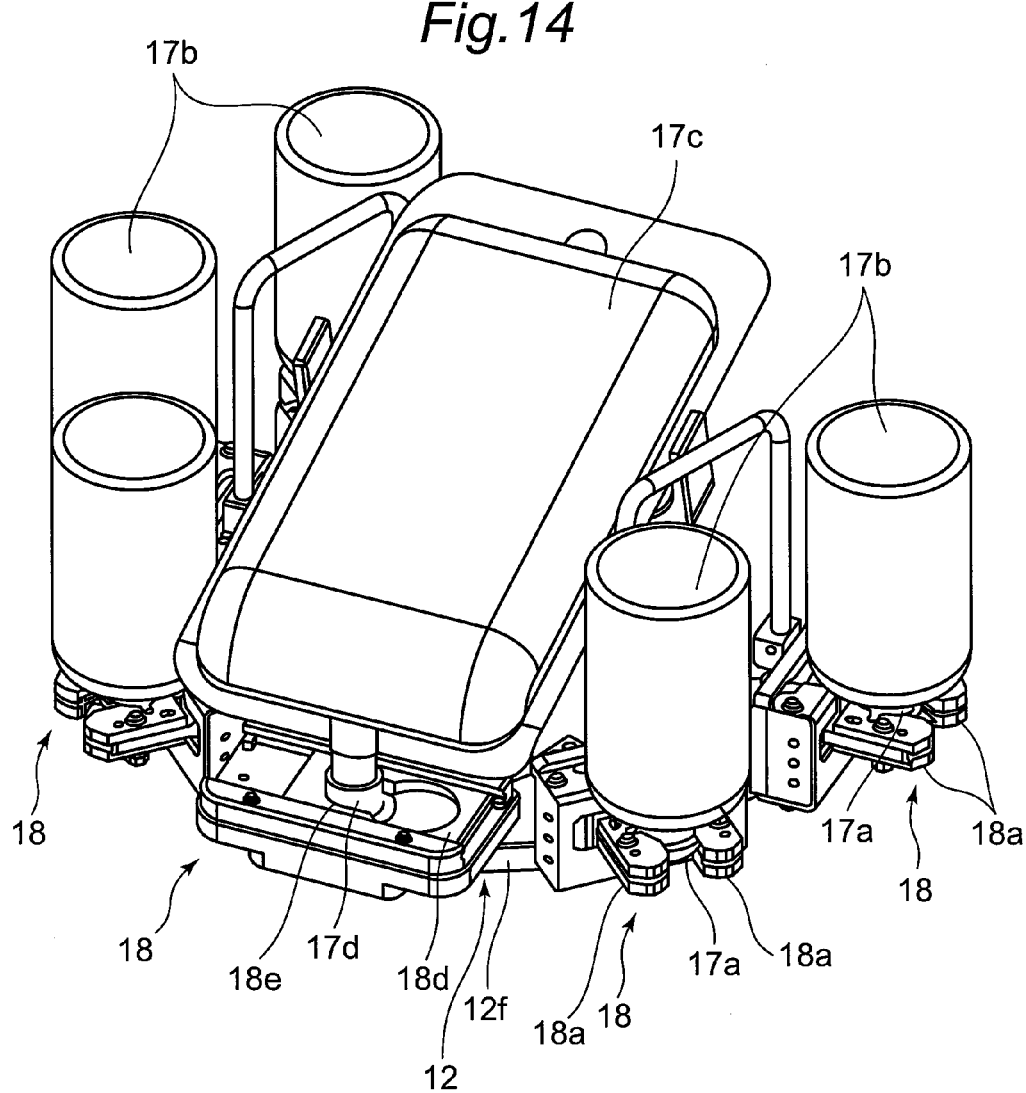
FIG. 14 is a perspective view illustrating the medicine cassette of the medicine mixing device according to the first embodiment of the present invention in a state where the medicine container is held.

Next, the operator places and sets the medicine cassette 12 holding the medicine container 17 on the first pedestal 13a of the lifting unit 13 being in the standby state at the lower position 15b of the medicine mixing device 10 (see FIG. 14). Specifically, the operator places and sets the medicine cassette 12 on the first pedestal 13a while fitting each of the pair of positioning pins 13d of the first pedestal 13a into each of the pair of position regulating holes 12d of the medicine cassette 12 to position the fixing unit 12f on the first pedestal 13a (see FIGS. 15 and 16). The operator depresses the setting completion button 24b of the operation panel 24 when the setting of the medicine cassette 12 to the first pedestal 13a is completed. These steps are included in the medicine cassette setting step, and are the preparatory operations before Step S14 of FIG. 10 is performed.

Next, when the preparatory operation is completed and the setting completion button 24b of the operation panel 24 is depressed, the transfusion preparatory operation of FIG. 10 is initiated under the control from the controlling section 100. That is, the controlling section 100 controls the driving of the fourth driving unit 13M of the lifting unit 13, so that the medicine cassette 12 together with the first pedestal 13a is, as illustrated in FIGS. 1, 5, and 16 to 19, lifted from the lower position 15b up to the middle position 15c of the main body 15 by the pair of parallel link mechanisms 13b of the lifting unit 13 (see Step S14 and FIGS. 16 to 19). At this time, since the medicine cassette 12 is lifted up by the pair of parallel link mechanisms 13b each of which includes a pair of one S-shaped member 13bS and one L-shaped member 13bL, the medicine cassette 12 is raised from the lower position 15b to the middle position 15c while maintaining the horizontal attitude thereof. In the first embodiment, in this Step S14, the first pedestal 13a is raised by the lifting unit 13 from the lower position 15b up to the middle position 15c along the forward surface 15a of the main body 15 in an arcuate path indicated by the arrow 32 of FIG. 5.

Next, the controlling section 100 controls operation of the fourth driving unit 13M so that the lifting-up operation of Step S14 is continued until the lifting-up of the medicine cassette 12 to the middle position 15c is completed (Step S15). That is, on the basis of the signals detected by the encoder 13Me in the fourth driving unit 13M, the controlling section 100 controls the driving of the motor 13Mm, so that the fourth driving unit 13M continues driving in Step S14 until the lifting-up operation of the medicine cassette 12 to the middle position 15c is completed. The processes of Steps S14 and S15 are included in a first step. The first step is one example of a lifting-up step of lifting the medicine cassette 12 from the lower position 15b up to the middle position 15c.

Figure 18:
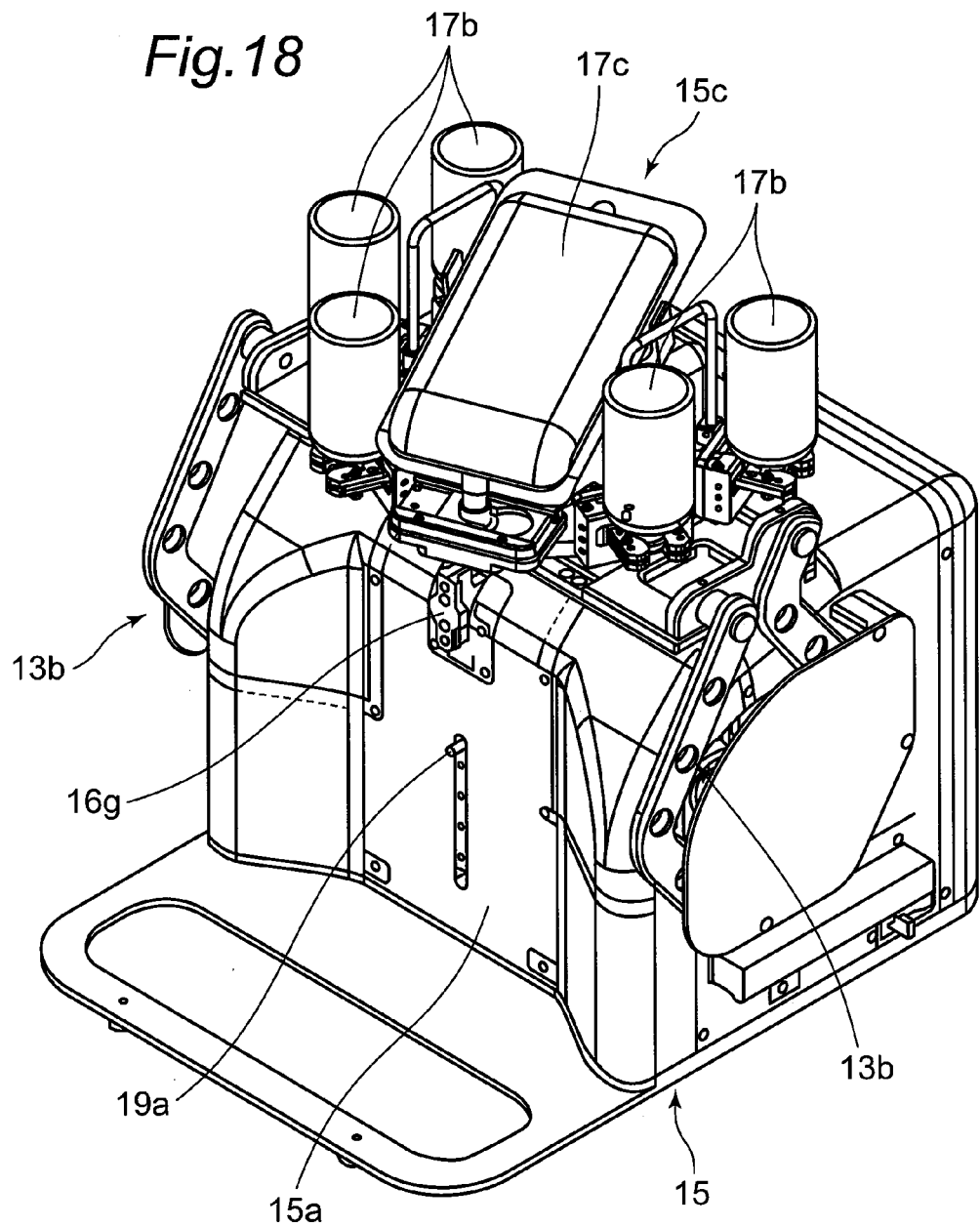
FIG. 18 is a perspective view of the medicine mixing device according to the first embodiment of the present invention in a state where the medicine cassette is positioned in the middle position.
Figure 19:
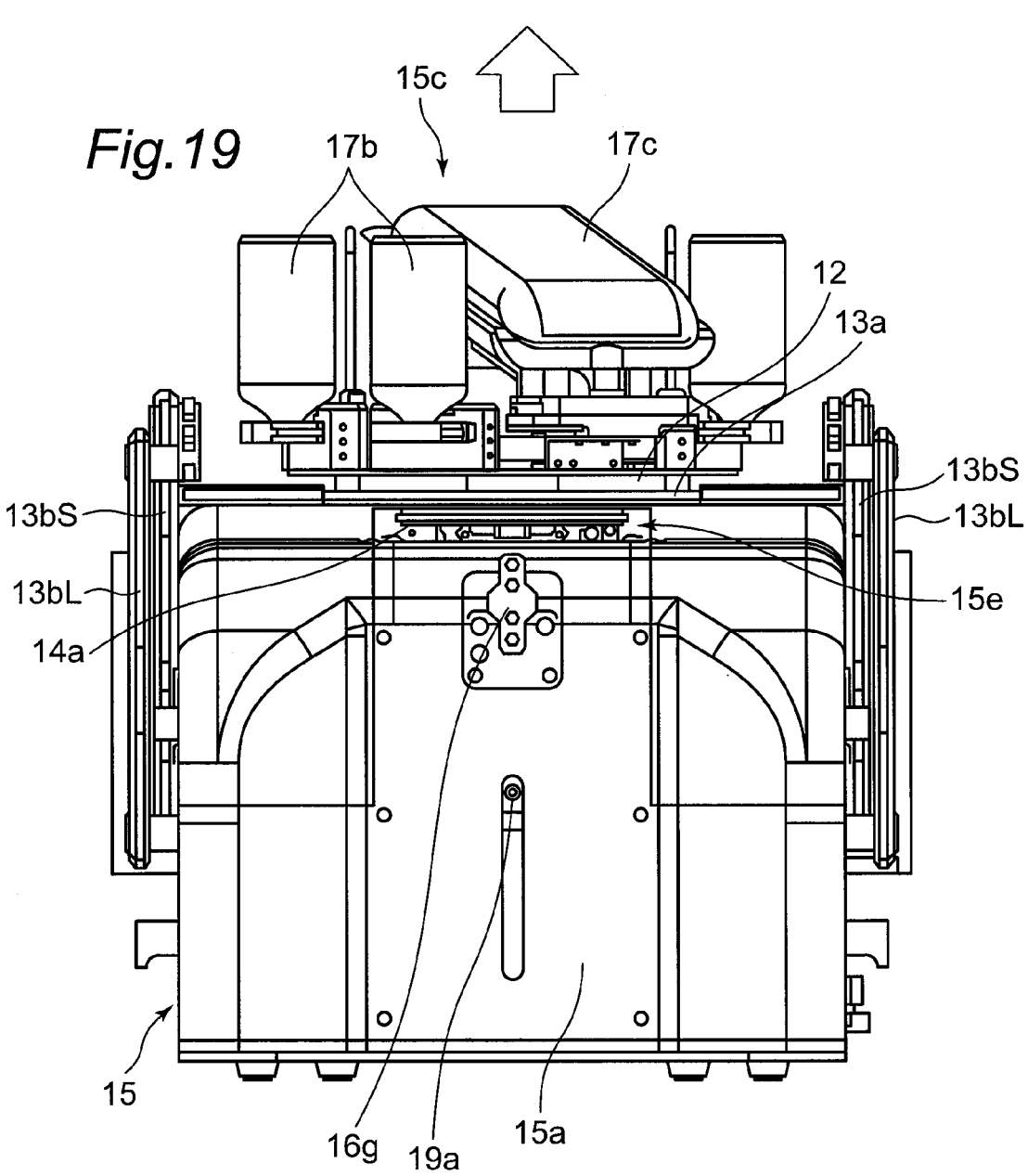
FIG. 19 is a perspective view of the medicine mixing device according to the first embodiment of the present invention in a state before the medicine cassette positioned in the middle position is reloaded from a first pedestal onto a second pedestal.

Next, when the lifting-up of the medicine cassette 12 to the middle position 15c of the main body 15 is completed (YES in Step S15), as illustrated in FIGS. 5, 18, and 19, the controlling section 100 controls the driving of the first driving unit 14U, so that the second pedestal 14a waited in a standby position 15e located below the first pedestal 13a of the lifting unit 13 is raised along the arrow 35 up to the middle position 15c where the medicine cassette 12 from the standby position 15e is received (Step S16). On the basis of the signals detected by the encoder of the fourth driving unit 13M, when the controlling section 100 detects that the reloading of the medicine cassette 12 from the first pedestal 13a to the second pedestal 14a is completed in the middle position 15c, the driving of the fourth driving unit 13M is stopped. At this time, the projection 14e on the front side of the second pedestal 14a passes through the notch 13e of the first pedestal 13a, and is brought into contact with the fixing unit 12f of the medicine cassette 12, so that the fixing unit 12f is lifted up and reloaded from the first pedestal 13a. When the controlling section 100 controls the driving of the first driving unit 14U, in the case where the controlling section 100 determines that a predetermined distance of raise has not been completed and thus the reloading of the medicine cassette 12 to the second pedestal 14a has not been completed, the second pedestal 14a is further raised by the first driving unit 14U under the control from the controlling section 100 in Step S16 (see NO in Step S17, Step S16 and FIGS. 18 and 19).

Next, when the controlling section 100 determines that the reloading of the medicine cassette 12 to the second pedestal 14a has been completed by means of the predetermined distance of the raise of the second pedestal 14a(YES in Step S17), before starting mixing the medicine, the second pedestal 14a is further raised by the first driving unit 14U under the control from the controlling section 100 in the vertical direction 31a (see FIG. 1) parallel to the arrow 35 (see FIG. 5B) up to the upper position 15d which is the home position. At this time, since the medicine cassette 12 is raised together with the second pedestal 14a, the port portion 17a of the medicine container 17 is raised up to the upper position 15d (Step S18).

Figure 20:
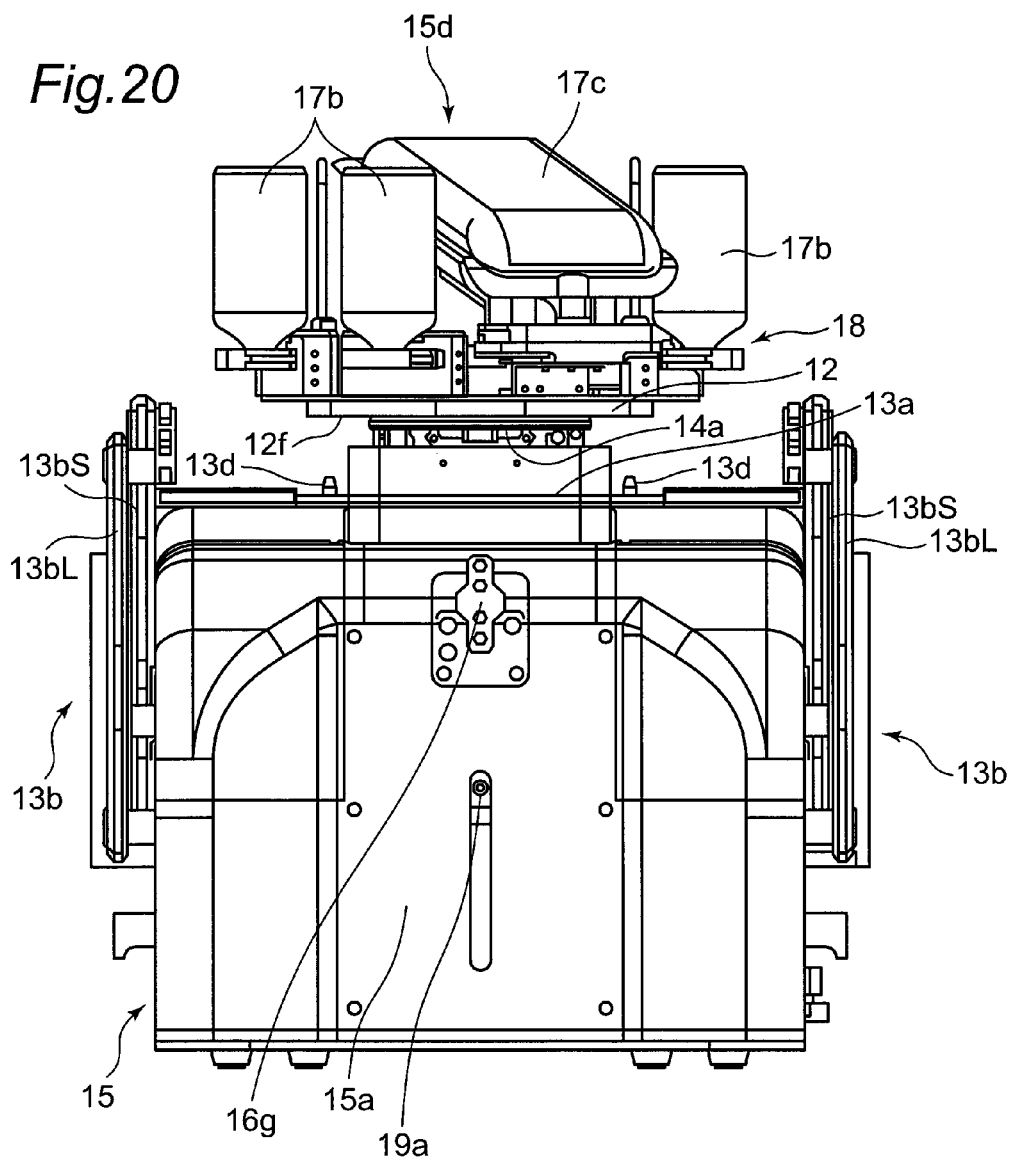
FIG. 20 is a perspective view of the medicine mixing device according to the first embodiment of the present invention in a state where the medicine cassette positioned in the middle position is reloaded from the first pedestal onto the second pedestal.

Next, under the control from the controlling section 100, the lifting-up operation of Step S18 is continued until the raise of the second pedestal 14a and the port portion 17a up to the upper position 15d is completed (see NO in Step S19, Step S18, and FIG. 19). Specifically, on the basis of the signals detected by the encoder of the first driving unit 14U, when the controlling section 100 detects that the raise of the second pedestal 14a and the port portion 17a up to the upper position 15d is completed, the driving of the first driving unit 14U is stopped. When the controlling section 100 determines that the second pedestal 14a has been raised up to the upper position 15d and when the controlling section 100 determines that the port portion 17a of the medicine container 17 has been disposed on the upper position 15d (Step S19, see FIG. 20), the preparatory operation the mixing operation of the medicine is completed. The processes from Steps S16 to S19 are included in a second step. The second step is a cassette delivering step, in which the medicine cassette 12 is delivered from the first pedestal 13a to the second pedestal 14a. The processes from Step S14 to Step S19 are included in the transfusion preparatory operation.

When the completion of the transfusion preparatory operation is determined in such a manner as described, under the control from the controlling section 100, the medicine mixing device 10 instructs the operator to mount the first holding portion 16 on the main body 15 by means, for example, of lighting up a lamp. In response to the instruction, the operator mounts the first holding portion 16 that holds the syringe 11 on the forward surface 15a of the main body 15. By virtue of this mounting, the coupling portion 16c of the first holding portion 16 is coupled to the driving pin 19a, thereby allowing the plunger 11b to move integrally with the driving pin 19a.

Next, when the mounting of the first holding portion 16 is completed and when the operator depresses the mounting completion button 24c of the operation panel 24, the medicine mixing device 10 initiates the transfusion operation of the FIG. 11 under the control from the controlling section 100. That is, the controlling section 100 controls the driving of the second driving unit 14R to rotate the medicine cassette 12 in forward and reverse direction with respect to the rotating direction 31b. By rotating in such a manner as described, the medicine container 17 subjected to sucking or discharging operation (intended medicine container) can be selected and disposed on the medicine extraction position 15g located directly above the needle 11a at the tip of the syringe 11 (Step S22 of the FIG. 11). Here, the selection of the medicine container 17 is determined on the basis of information on a prescription obtained, for example, from a server in the hospital (not illustrated), or information inputted by the operator (see Step S22-0 of FIG. 11, i.e., the step one step before Step S22 of FIG. 11). Here, the controlling section 100 controls the driving of the second driving unit 14R to move the medicine container 17 by rotating the medicine cassette 12 in the rotating direction 31b until the selection of the intended medicine container 17 is completed (NO in Step S23, Step S22). For example, when the types and internal capacities of all medicine containers 17 set on the medicine cassette 12 are stored beforehand in a storage section 101, appropriate medicine is selected from the storage section 101 on the basis of information on the prescription or information inputted by the operator, then the difference between the position of the medicine container 17 containing the medicine and the position opposing the needle 11a of the syringe 11 (medicine extraction position 15g) is calculated by an arithmetic operation section 102, and the amount of the rotation of the medicine cassette 12 may be controlled by driving the second driving unit 14R on the basis of the calculated result. The processes from Steps S21 to S23 are included in a fifth step. The fifth step is one example of a medicine-container selecting step, in which the intended medicine container is selected, and the fifth step is performed at at least one of before and after the third step, and before the fourth step, which will be described later.

Next, when the selection and placement of the medicine container 17 subjected to sucking or discharging operation is completed (YES in Step S23), the first driving unit 14U moves the medicine cassette 12 together with the second pedestal 14a downward in the vertical direction 31a from the upper position 15d to cause the needle 11a to puncture the port portion 17a of the medicine container 17 positioned in the medicine extraction position 15g (Step S24). Here, the controlling section 100 controls the driving of the first driving unit 14U to move the medicine cassette 12 downward in the vertical direction 31a until the puncture of the needle 11a into the intended medicine container 17 is completed (NO in Step S25, Step S24). That is, on the basis of signals detected by the encoder 14Ue in the first driving unit 14U, the controlling section 100 controls the driving of the motor 14Um, so that the controlling section 100 continues controlling the driving of the first driving unit 14U in Step S24 until the puncture of the needle 11a into the intended medicine container 17 positioned from the upper position 15d to the medicine extraction position 15g is completed (in other words, until a predetermined distance of the downward movement of the medicine cassette 12 is completed). The processes from Steps S24 and S25 are included in a third step. The third step is a cassette moving-down step, in which the medicine cassette 12 is moved downward for inserting the needle 11a of the syringe 11 into the medicine container 17.

Next, the controlling section 100 determines that the needle 11a is punctured into the port portion 17a of the medicine container 17 subjected to sucking or discharging operation that is positioned in the medicine extraction position 15g (YES in Step 25). When the puncture is determined, the controlling section 100 controls the driving of the fifth driving unit 19M to initiate either one of the following operations: sucking the medicine from the medicine container 17 subjected to sucking operation to the syringe 11 by virtue of downward movement of the plunger 11b, or discharging the medicine from the syringe 11 to the medicine container 17 subjected to discharging operation by virtue of upward movement of the plunger 11b (Step S26). Here, the controlling section 100 controls the driving of the fifth driving unit 19M to continue sucking or discharging the medicine until the predetermined amount of medicine is fully sucked to or discharged from the syringe 11 (NO in Step S27, Step 26). As a specific example, the case where the medicine is sucked from the vial bottle 17b or the like to the syringe 11, or the case where the medicine is discharged from the syringe 11 to the infusion bag 17c or the like is considered. In this case, first, in the medicine mixing device 10, the controlling section 100 controls the driving of the second driving unit 14R to drive and rotate the medicine cassette 12, and then, as illustrated in FIG. 5, the medicine container 17 to be used for mixing or transfusing is disposed on the medicine extraction position 15g located directly above the needle 11a of the syringe 11. After that, the controlling section 100 controls the driving of the first driving unit 14U to move the medicine cassette 12 downward along the arrow 35 so that the needle 11a at the tip of the syringe 11 held by the first holding portion 16 is inserted into the port portion 17a of the medicine container 17. When the needle 11a is inserted into the medicine container 17, the controlling section 100 controls the driving of the fifth driving unit 19M to move the plunger 11b of the syringe 11 downward along the arrow 33, so that the predetermined amount of the medicine is sucked from the vial bottle 17b or the like to the syringe 11 (or the medicine is discharged from the syringe 11 to the infusion bag 17c or the like). Herein, description is be given using the vial bottle 17b or the infusion bag 17c, which is used at higher frequencies mixing a plurality of medicines, as the medicine container 17.

When the controlling section 100 determines that the predetermined amount of medicine is fully sucked to or discharged from the syringe 11 (YES in Step 27), the controlling section 100 controls the driving of the first driving unit 14U to move the medicine cassette 12 up to the upper position 15d (NO in Step S29, Step S28). After the controlling section 100 determines that the medicine cassette 12 has been moved up to the upper position 15d (YES in Step S29), the controlling section 100 appropriately controls the driving of the second driving unit 14R, the first driving unit 14U, and the fifth driving unit 19M to continuously repeat the operations of Steps S22 to S29 for all the intended medicines which are subjected to mixing operation (Step S30). In other words, in Step S30, if the mixing of all the intended medicine containers 17 has not been completed (NO in Step S30 of the FIG. 11), then return to Step S22 to repeat the operations of Steps S22 to S29. In the case where sucking or discharging of intended medicine in another medicine container 17 is performed, under the control from the controlling section 100, the first driving unit 14U moves the medicine cassette 12 up to the upper position 15d to remove the needle 11a from the medicine container 17, then the second driving unit 14R rotates the medicine cassette 12 in forward and reverse direction with respect to the rotating direction 31b to dispose the another medicine container 17 on the syringe 11. After the first driving unit 14U is driven to move the medicine cassette 12 downward to insert the needle 11a into the medicine container 17, the fifth driving unit 19M drives the plunger 11b of the syringe 11 to perform the sucking or discharging of the predetermined amount of another intended medicine. The processes from Step S22 to this Step S30 are included in the transfusion operation.

Here, the operator may visually determine (check) whether or not the predetermined amount of the medicine has been fully sucked to or discharged from the syringe 11 in Step S27. In the case of visual check by the operator, upon completion of Step S27, the operation of the medicine mixing device 10 is temporarily suspended, and based on whether or not a visual check by the operator is necessary, the operator, for example, instructs the controlling section 100 to perform fine adjustments to the amount of sucking or the amount of discharging.

It should be noted that during the processes from Step S22 to Step S29, the medicine contained in the medicine container 17 may be stirred and dissolved in such a manner that under the control from the controlling section 100, the first driving unit 14U or the second driving unit 14R drives the medicine cassette 12 in the vertical direction 31a or in the rotating direction 31b. As described above, by stirring and dissolving the medicine during the mixing operation of the medicine, the medicine in the medicine containers 17 can be efficiently mixed in a short time.

When mixing operation for all the intended medicine containers 17 is completed (YES in Step S30 of FIG. 11), by the control from the controlling section 100, the medicine mixing device 10 instructs the operator to remove the first holding portion 16 from the main body 15 by means, for example, of lighting up the lamp (preparatory operation prior to Step S35 of FIG. 12). When the removal of the first holding portion 16 from the main body 15 by the operator is completed, the operator depresses the removal completion button 24d of the operation panel 24 (preparatory operation prior to Step S35 of FIG. 12).

When the removal completion button 24d is depressed, the transfusion end operation in FIG. 12 is initiated by the control from the controlling section 100. That is, the controlling section 100 controls the driving of the first driving unit 14U to move the medicine cassette 12 from the upper position 15d down to the middle position 15c (Step S35 of FIG. 12). Here, the second pedestal 14a keeps moving downward until the downward movement of the second pedestal 14a to the middle position 15c where the medicine cassette 12 can be delivered to the first pedestal 13a, and the release (disengagement) of the medicine cassette 12 from the second pedestal 14a are determined (NO in Step S36, Step S35). The processes of Steps S35 and S36 are included in a sixth step. The sixth step is a cassette releasing step, in which the medicine cassette 12 is released from the second pedestal 14a.

When the completion of the delivery and the release of the medicine cassette 12 is determined (YES in Step S36), the controlling section 100 controls the driving of the fourth driving unit 13M so that the first pedestal 13a lifts the medicine cassette 12 downward from the position in proximity to the middle position 15c of the main body 15 to the lower position 15b (Step S40). Here, the lifting unit 13 includes the pair of parallel link mechanisms 13b, and thus is capable of lifting down the medicine cassette 12, while maintaining the horizontal attitude of the medicine cassette 12. This process of Step S40 is a cassette lifting-down step, which is one example of a seventh step. The processes from Step S35 to this Step S40 are included in the transfusion end operation. The operator subsequently removes the medicine cassette 12 from the first pedestal 13a of the lifting unit 13, and depresses the operation completion button 24f.

Next, when the operation completion button 24f is depressed, the lifting unit 13 moves the first pedestal 13a of the lifting unit 13 up to the position in proximity to the middle position 15c. When the raise of the first pedestal 13a up to the middle position 15c is completed, a series of medicine mixing operation is ended.

It should be noted that the step of attaching the first holding portion 16 and Steps S22 and S23 of selecting the medicine container 17, are the steps performed as needed, and thus may be omitted when deemed unnecessary.

Also, a return operation to the standby position 15e of the second pedestal 14a may be inserted after YES in Step S36. In this case, the controlling section 100 controls the driving of the first driving unit 14U to move the second pedestal 14a downward to the standby position 15e (Step S37). The operation is continued until the downward movement of the second pedestal 14a to the standby position 15e is completed (NO in Step S38, Step S37), and when the completion of the downward movement of the second pedestal 14a to the standby position 15e is determined (YES in Step S38), the operator depresses the dispensing button 24e of the operation panel 24 instructing the dispensing of the medicine cassette 12 (Step S39). At this time, depressing the dispensing button 24e may lead to Step S40.

It should be noted that here, such steps as the preparatory operation step before Step S14, the step of attaching the first holding portion 16 to the main body 15 after Step S19, and the step of removing the first holding portion 16 from the main body 15 before Step S35 are performed manually by the operator, and other steps (such as the steps in FIGS. 10 to 12) are automatically operated by the medicine mixing device 10.

The medicine mixing device 10 of the first embodiment having such a configuration as described above provides a safe handling of a plurality of medicines, and also allows operators to efficiently perform medicine mixing and transfusing operation in a limited work space. Further, the medicine mixing device 10 of the first embodiment has the characteristic shaped parallel link mechanisms 13b, by which the medicine mixing device 10 of the first embodiment can be compact, yet allowing operators to easily handle a plurality of medicines only at hand. Therefore, the medicine mixing device 10 of the first embodiment is particularly advantageous when mixing operation is performed at a limited space in a hospital, or the like.

It should be noted that in the first embodiment, the medicine cassette 12 and the first holding portion 16 are configured to be detachable from the main body 15, which facilitates cleaning, maintenance, and replacement of the medicine cassette 12 or the first holding portion 16.

Further, the second holding portion 18 may have a centering retention mechanism, in such a manner that the recesses 18b on each opposing face of the pair of the fixing plate 18a is formed in a V-valley shape, and a pair of the recesses 18b holds the cylindrical-shaped port portions 17a and 17d therebetween, such that the center of the port portions 17a and 17d automatically coincides with the center position of the pair of the recesses 18b formed between the pair of the fixing plates 18a. This configuration ensures that the position of the second holding portion 18 can be adjusted with the position of the tip of the needle 11a of the syringe 11, thereby providing a well-defined insertion of the needle tip of the syringe 11 into the center of the port portion 17a of the medicine container 17.

As regards vertical driving mechanism, it is not limited to the first driving unit 14, in which the medicine container 17 vertically moves with respect to the fixed syringe 11, and instead, a mechanism may also be employed, in which the syringe 11 moves vertically with respect to the fixed medicine container 17. Such a mechanism may include a ball screw that rotates in forward and reverse direction by the rotation of a motor, and a nut member that moves up and down with being threadably engaged with the ball screw, and by fixing the syringe 11 to the nut member, the syringe 11 can be vertically moved by the rotation of the motor in forward and reverse direction.

By properly combining the arbitrary embodiment (s) or modification(s) of the aforementioned various embodiments and modifications, the effects possessed by the embodiment (s) or modification(s) can be produced.

Although the present invention has been fully described in connection with the preferable embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

INDUSTRIAL APPLICABILITY

The medicine transfusion apparatus and the medicine transfusion method according to the present invention are capable of being set or operated in a limited space, capable of efficiently transfusing a medicine, and thus are advantageous in transfusing operation of a medicine performed by nurses and pharmacists in hospitals.

The invention claimed is:

1. A medicine transfusion apparatus transfusing a medicine between a medicine container and a syringe by the syringe, the medicine transfusion apparatus comprising:
  a medicine cassette that holds the medicine container;
  a lifting unit that moves the medicine cassette upward and downward between a middle position on an upper portion and a lower position of a main body along an arcuate path while maintaining a horizontal attitude of the medicine cassette using a pair of parallel link mechanisms;
  a first holding portion that is capable of holding the syringe and is detachably mounted to the main body;
  a first driving unit that relatively moves the medicine cassette and the first holding portion so that a needle of the syringe held by the first holding portion is inserted into the medicine container; and
  a second driving unit that drives a plunger of the syringe to transfuse the medicine between the syringe and the medicine container.

2. The medicine transfusion apparatus according to claim 1, wherein
  each of the pair of parallel link mechanisms comprises an L-shaped link and an S-shaped link, one end of each of the links is coupled to the main body, and an other end of each of the links is coupled to a first pedestal of the lifting unit holding the medicine cassette.

3. The medicine transfusion apparatus according to claim 2, wherein
in the parallel link mechanism, the L-shaped link is disposed vertically below the S-shaped link in the lower position.

4. The medicine transfusion apparatus according to claim 3, wherein
in the parallel link mechanism, a line connecting between portions each being coupled to the main body and to the first pedestal at both ends of the L-shaped link, and a line connecting between portions each being coupled to the main body and to the first pedestal at both ends of the S-shaped link are parallel to each other in the lower position.

5. The medicine transfusion apparatus according to claim 4, wherein
in the parallel link mechanism, a line connecting between portions each being coupled to the main body and to the first pedestal at the both ends of the L-shaped link, and a line connecting between portions each being coupled to the main body and to the first pedestal at the both ends of the S-shaped link are parallel to each other in the middle position.

6. The medicine transfusion apparatus according to claim 1, wherein
the lifting unit moves the medicine cassette upward and downward between the middle position and the lower position along a forward surface of the main body and along the arcuate path by a rotational movement of the pair of parallel link mechanisms.

7. The medicine transfusion apparatus according to claim 1, further comprising a first driving unit that drives the medicine cassette in a vertical direction or in a rotating direction in a plane that intersects the vertical direction, wherein
in the first driving unit, the medicine cassette reloaded from the first pedestal of the lifting unit to a second pedestal of the first driving unit in the middle position is driven in the vertical direction or in the rotating direction, so that the medicine container held by the medicine cassette is positioned at a medicine extraction position opposing the needle of the syringe held by the first holding portion.

8. The medicine transfusion apparatus according to claim 7, wherein
the medicine cassette includes an arc-shaped member, and has a structure, in which a plurality of the medicine containers are capable of being disposed in a circumferential direction.

9. The medicine transfusion apparatus according to claim 1, wherein
the medicine cassette has a second holding portion that holds a port portion of the medicine container, and comprises a centering retention mechanism that makes a center of the port portion correspond to a position of the needle of the syringe.

10. The medicine transfusion apparatus according to claim 1, wherein
the medicine cassette and the first holding portion are adapted to be detachable from the main body.

11. A medicine transfusion method comprising:
a first step of moving a medicine cassette holding a medicine container upward from a lower position of a main body to a middle position on an upper portion of the main body along an arcuate path while maintaining a horizontal attitude of the medicine cassette by a lifting unit utilizing a pair of parallel link mechanisms;
a second step of reloading the medicine cassette from a first pedestal of the lifting unit to a second pedestal of a first driving unit in the middle position after the first step;
a third step of inserting a needle of a syringe held by a first holding portion into the medicine container held by the medicine cassette after the second step; and
a fourth step of driving a plunger of the syringe to transfuse a medicine between the syringe and the medicine container after the third step.

12. The medicine transfusion method according to claim 11, wherein
the lifting unit moves the medicine cassette upward between the middle position and the lower position along a forward surface of the main body and along the arcuate path by a rotational movement of the pair of parallel link mechanisms in the first step.

13. The medicine transfusion method according to claim 11, further comprising
a fifth step of selecting a medicine container performing a transfusion operation, among a plurality of the medicine containers held by the medicine cassette, the fifth step being performed at at least one of before and after the third step, and before the fourth step.

14. The medicine transfusion method according to claim 11, wherein
the medicine cassette is driven in a vertical direction or in a rotating direction to stir and dissolve the medicine in the medicine container after the fourth step.

* * * * *